US008008048B2

(12) United States Patent
Nonaka et al.

(10) Patent No.: US 8,008,048 B2
(45) Date of Patent: Aug. 30, 2011

(54) L-CYSTEINE-PRODUCING BACTERIUM AND A METHOD FOR PRODUCING L-CYSTEINE

(75) Inventors: Gen Nonaka, Kawasaki (JP); Kazuhiro Takumi, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 195 days.

(21) Appl. No.: 12/397,666

(22) Filed: Mar. 4, 2009

(65) Prior Publication Data
US 2009/0226983 A1 Sep. 10, 2009

(30) Foreign Application Priority Data

Mar. 6, 2008 (JP) ................................. 2008-056362

(51) Int. Cl.
*C12P 13/12* (2006.01)
*C07K 14/00* (2006.01)
*C07H 21/00* (2006.01)
*C12N 1/21* (2006.01)
*C12N 15/00* (2006.01)
*C12P 21/00* (2006.01)

(52) U.S. Cl. ................ 435/113; 435/252.3; 435/252.33; 435/69.1; 435/440; 530/350; 536/23.1

(58) Field of Classification Search .................. 435/113, 435/69.1, 320.1, 252.3, 252.33; 536/23.2
See application file for complete search history.

(56) References Cited

U.S. PATENT DOCUMENTS

| | | | |
|---|---|---|---|
| 5,618,716 A | 4/1997 | Burlingame | |
| 5,856,148 A | 1/1999 | Burlingame | |
| 5,972,663 A | 10/1999 | Winterhalter et al. | |
| 6,218,168 B1 | 4/2001 | Leinfelder et al. | |
| 7,348,037 B2 | 3/2008 | Buchholz et al. | |
| 2003/0077766 A1 | 4/2003 | Takagi et al. | |
| 2003/0186393 A1 | 10/2003 | Takagi et al. | |
| 2004/0038352 A1 | 2/2004 | Maier | |
| 2005/0009162 A1 | 1/2005 | Maier et al. | |
| 2005/0112731 A1 | 5/2005 | Kashiwagi et al. | |
| 2005/0124049 A1 | 6/2005 | Ziyatdinov et al. | |
| 2005/0221453 A1 | 10/2005 | Takagi et al. | |
| 2008/0076163 A1 | 3/2008 | Takagi et al. | |
| 2008/0193470 A1* | 8/2008 | Masignani et al. | ........ 424/185.1 |

FOREIGN PATENT DOCUMENTS

| | | |
|---|---|---|
| CA | 2386539 | 4/2007 |
| JP | 11-155571 | 6/1999 |
| JP | 2002-233384 | 8/2002 |
| JP | 2003-169668 | 6/2003 |
| JP | 2005-245311 | 9/2005 |
| JP | 2005-287333 | 10/2005 |
| WO | WO01/27307 | 4/2001 |

OTHER PUBLICATIONS

Branden et al., Introduction to Protein Structure, Garland Publishing Inc., New York, p. 247, 1991.*
Zhou et al., Cell Mol Life Sci 63(19-20):2260-2290, 2006.*
Kozak, M., Gene 234:187-208, 1999.*
Sousa et al., Microbiology 148(Pt5):1291-1303, 2002.*
Awano, N., et al., "Effect of cysteine desulfhydrase gene disruption on L-cysteine overproduction in *Escherichia coil*," Appl. Microbiol. Biotechnol. 2003;62:239-243.
Awano, N., et al., "Identification and Functional Analysis of *Escherichia coli* Cysteine Desulfhydrases," Appl. Environmen. Microbiol. 2005;71(7):4149-4152.
Daβler, T., et al., "Identification of a major facilitator protein from *Escherichia coli* involved in efflux of metabolites of the cysteine pathway," Molecular Microbiol. 2000;36(5):1101-1112.
Dominy, J. E., et al., "Identification and Characterization of Bacterial Cysteine Dioxygenases: a New Route of Cysteine Degradation for Eubacteria," J. Bacteriol. 2006;188(15):5561-5569.
EcoCyc (BioCyc Home Page, Summary of *Escherichia coli*, Strain K-12, version 11.6, *E. coli* K-12 Gene: *yhaM*, http://biocyc.org/ECOLI/NEW-IMAGE?type=GENE&object=G7622).
Flatley, J., et al., "Transcriptional Responses of *Escherichia coli* to D-Nitrosoglutathione under Defined Chemostat Conditions Reveal Major Changes in Methionine Biosynthesis," J. Biol. Chem. 2005;280(11):10065-10072.
Pae, K. M., et al., "Kinetic Properties of a L-Cysteine Desulfhydrase-Deficient Mutant in the Enzymatic Formation of L-Cysteine from D,L-ATC," Biotechnol. Lett. 1992;14(12):1143-1148.
Soutourina, J., et al., "Role of D-Cysteine Desulfhydrase in the Adaptation of *Escherichia coli* to D-Cysteine," J. Biol. Chem. 2001;276(44):40864-40872.
Tchong, S-I., et al., "L-Cysteine Desulfidase: An [4Fe-4S] Enzyme Isolated from *Methanocaldococcus jannaschii* That Catalyzes the Breakdown of L-Cysteine into Pyruvate, Ammonia, and Sulfide," Biochem. 2005;44(5):1659-1670.
Wada, M., et al., "Purification, characterization and identification of cysteine desulfhydrase of *Corynebacterium glutamicum*, and its relationship to cysteine production," FEMS Microbiol. Lett. 2002;217:103-107.
Zdych, E., et al., "MalY of *Escherichia coli* Is an Enzyme with the Activity of βC-S Lyase (Cystathionase)," J. Bacteriol. 1995;177(17):5035-5039.
Database UniProt [Online], Nov. 1, 1995, "RecName: Full=UPF0597 protein yhaM;" retrieved from EBI accession No. UNIPROT: P42626, Database accession No. P42626. Denk, D., et al., "L-Cysteine Biosynthesis in *Escherichia coli*: Nucleotide Sequence and Expression of the Serine Acetyltransferase (*cysE*) Gene from the Wild-type and a Cysteine-excreting Mutant," J. Gen. Microbiol. 1987;133:515-525.
Takagi, H., et al., "Overproduction of L-Cysteine and L-Cystine by expression of genes for feedback inhibition-insensitive serine acetyltransferase from *Arabidopsis thaliana* in *Escherichia coli*," FEMS Microbiol. Lett. 1999;179:453-459.
Wada, M., et al., "Metabolic pathways and biotechnological production of L-cysteine," Appl. Microbiol. Biotechnol. 2006;73:48-54.
European Search Report for European Patent App. No. 09003106.3 (Nov. 11, 2009).
Flatley, J., et al., "Transcriptional Responses of *Escherichia coli* to S-Nitrosoglutathione under Defined Chemostat Conditions Reveal Major Changes in Methionine Biosynthesis," J. Biol. Chem. 2005;280(11):10065-10072.

* cited by examiner

*Primary Examiner* — Delia Ramirez
(74) *Attorney, Agent, or Firm* — Shelly Guest Cermak; Cermak Nakajima LLP

(57) ABSTRACT

The present invention provides a bacterium belonging to the family Enterobacteriaceae which has L-cysteine-producing ability and has been modified to decrease the activity of the protein encoded by the yhaM gene. This bacterium is cultured in a medium, and L-cysteine, L-cystine, their derivatives, or a mixture thereof is collected from the medium.

6 Claims, 5 Drawing Sheets

SEQUENCE LISTING

```
<160> NUMBER OF SEQ ID NOS: 31

<210> SEQ ID NO 1
<211> LENGTH: 1311
<212> TYPE: DNA
<213> ORGANISM: Escherichia coli
<220> FEATURE:
<221> NAME/KEY: CDS
<222> LOCATION: (1)..(1311)

<400> SEQUENCE: 1 atg ttt gat tcg act tta aat ccg tta tgg cag cgt tac atc ctc gcc    48
Met Phe Asp Ser Thr Leu Asn Pro Leu Trp Gln Arg Tyr Ile Leu Ala
```

| | | | | | | | | | | | | | | | | |
|---|---|---|---|---|---|---|---|---|---|---|---|---|---|---|---|---|
| 1 | | | | 5 | | | | | 10 | | | | | 15 | | |
| gtt | cag | gag | gaa | gta | aaa | ccg | gcg | ctg | gga | tgt | act | gaa | ccg | att | tca | 96 |
| Val | Gln | Glu | Glu | Val | Lys | Pro | Ala | Leu | Gly | Cys | Thr | Glu | Pro | Ile | Ser | |
| | | 20 | | | | | 25 | | | | | 30 | | | | |
| ctg | gcg | ctg | gcg | gcg | gcg | gtt | gct | gcg | gca | gaa | ctg | gaa | ggt | ccg | gtt | 144 |
| Leu | Ala | Leu | Ala | Ala | Ala | Val | Ala | Ala | Ala | Glu | Leu | Glu | Gly | Pro | Val | |
| | | | 35 | | | | | 40 | | | | | 45 | | | |
| gaa | cgt | gta | gaa | gcc | tgg | gtt | tcg | cca | aat | ctg | atg | aag | aac | ggt | ctg | 192 |
| Glu | Arg | Val | Glu | Ala | Trp | Val | Ser | Pro | Asn | Leu | Met | Lys | Asn | Gly | Leu | |
| 50 | | | | | 55 | | | | | 60 | | | | | | |
| ggc | gtc | acc | gtt | ccc | ggc | acg | gga | atg | gtg | ggg | ctg | ccg | att | gcg | gcg | 240 |
| Gly | Val | Thr | Val | Pro | Gly | Thr | Gly | Met | Val | Gly | Leu | Pro | Ile | Ala | Ala | |
| 65 | | | | | 70 | | | | | 75 | | | | | 80 | |
| gcg | ctg | ggg | gcg | tta | ggt | gga | aat | gcc | aac | gcc | ggg | ctg | gaa | gtg | ctg | 288 |
| Ala | Leu | Gly | Ala | Leu | Gly | Gly | Asn | Ala | Asn | Ala | Gly | Leu | Glu | Val | Leu | |
| | | | | 85 | | | | | 90 | | | | | 95 | | |
| aaa | gac | gca | aca | gcg | cag | gca | att | gcc | gat | gcc | aaa | gca | ctg | ctg | gcg | 336 |
| Lys | Asp | Ala | Thr | Ala | Gln | Ala | Ile | Ala | Asp | Ala | Lys | Ala | Leu | Leu | Ala | |
| | | | 100 | | | | | 105 | | | | | 110 | | | |
| gcg | ggg | aaa | gtc | tcc | gtt | aag | atc | cag | gaa | cct | tgc | gat | gaa | atc | ctc | 384 |
| Ala | Gly | Lys | Val | Ser | Val | Lys | Ile | Gln | Glu | Pro | Cys | Asp | Glu | Ile | Leu | |
| | | 115 | | | | | 120 | | | | | 125 | | | | |
| ttc | tca | cgc | gcc | aaa | gtc | tgg | aac | ggt | gag | aag | tgg | gcg | tgt | gtc | acc | 432 |
| Phe | Ser | Arg | Ala | Lys | Val | Trp | Asn | Gly | Glu | Lys | Trp | Ala | Cys | Val | Thr | |
| 130 | | | | | 135 | | | | | 140 | | | | | | |
| atc | gtc | ggc | ggg | cat | acc | aac | att | gtg | cat | atc | gag | acg | cac | gat | ggt | 480 |
| Ile | Val | Gly | Gly | His | Thr | Asn | Ile | Val | His | Ile | Glu | Thr | His | Asp | Gly | |
| 145 | | | | | 150 | | | | | 155 | | | | | 160 | |
| gtg | gtg | ttt | acc | cag | cag | gcg | tgt | gtg | gca | gag | ggc | gag | caa | gag | tct | 528 |
| Val | Val | Phe | Thr | Gln | Gln | Ala | Cys | Val | Ala | Glu | Gly | Glu | Gln | Glu | Ser | |
| | | | | 165 | | | | | 170 | | | | | 175 | | |
| ccg | ctg | acg | gtg | ctt | tcc | aga | acg | acg | ctg | gct | gag | atc | ctg | aag | ttc | 576 |
| Pro | Leu | Thr | Val | Leu | Ser | Arg | Thr | Thr | Leu | Ala | Glu | Ile | Leu | Lys | Phe | |
| | | | 180 | | | | | 185 | | | | | 190 | | | |
| gtc | aat | gaa | gtc | ccg | ttt | gcg | gcg | atc | cgc | ttt | att | ctc | gat | tcc | gcg | 624 |
| Val | Asn | Glu | Val | Pro | Phe | Ala | Ala | Ile | Arg | Phe | Ile | Leu | Asp | Ser | Ala | |
| | | 195 | | | | | 200 | | | | | 205 | | | | |
| aag | cta | aat | tgt | gcg | tta | tcg | cag | gaa | ggt | ttg | agc | ggt | aag | tgg | ggg | 672 |
| Lys | Leu | Asn | Cys | Ala | Leu | Ser | Gln | Glu | Gly | Leu | Ser | Gly | Lys | Trp | Gly | |
| 210 | | | | | 215 | | | | | 220 | | | | | | |
| ctg | cat | att | ggc | gcg | acg | ctg | gaa | aaa | cag | tgc | gag | cgc | ggt | ttg | ctg | 720 |
| Leu | His | Ile | Gly | Ala | Thr | Leu | Glu | Lys | Gln | Cys | Glu | Arg | Gly | Leu | Leu | |
| 225 | | | | | 230 | | | | | 235 | | | | | 240 | |
| gcg | aaa | gat | ctc | tct | tca | tcc | att | gtg | att | cgt | acc | agc | gcg | gca | tcc | 768 |
| Ala | Lys | Asp | Leu | Ser | Ser | Ser | Ile | Val | Ile | Arg | Thr | Ser | Ala | Ala | Ser | |
| | | | | 245 | | | | | 250 | | | | | 255 | | |
| gat | gcg | cgt | atg | ggc | ggc | gct | acg | ctt | ccg | gct | atg | agt | aac | tcc | ggc | 816 |
| Asp | Ala | Arg | Met | Gly | Gly | Ala | Thr | Leu | Pro | Ala | Met | Ser | Asn | Ser | Gly | |
| | | 260 | | | | | 265 | | | | | 270 | | | | |
| tcg | ggt | aac | cag | ggg | att | acc | gca | aca | atg | cct | gtg | gtg | gta | gca | 864 | |
| Ser | Gly | Asn | Gln | Gly | Ile | Thr | Ala | Thr | Met | Pro | Val | Val | Val | Ala | | |
| | | 275 | | | | | 280 | | | | | 285 | | | | |
| gaa | cac | ttc | gga | gcg | gat | gat | gaa | cgg | ctg | gcg | cgt | gcg | ctg | atg | ctt | 912 |
| Glu | His | Phe | Gly | Ala | Asp | Asp | Glu | Arg | Leu | Ala | Arg | Ala | Leu | Met | Leu | |
| | | 290 | | | | | 295 | | | | | 300 | | | | |
| tcg | cat | ttg | agc | gca | att | tac | atc | cat | aac | cag | tta | ccg | cgt | ttg | tct | 960 |
| Ser | His | Leu | Ser | Ala | Ile | Tyr | Ile | His | Asn | Gln | Leu | Pro | Arg | Leu | Ser | |
| 305 | | | | | 310 | | | | | 315 | | | | | 320 | |
| gcg | ctg | tgt | gcc | gca | acg | acc | gca | atg | ggg | gcc | gcc | gcc | ggg | atg | | 1008 |
| Ala | Leu | Cys | Ala | Ala | Thr | Thr | Ala | Ala | Met | Gly | Ala | Ala | Ala | Gly | Met | |

```
                    325                 330                 335
gca tgg ctg gtg gat ggg cgt tat gaa acc atc tcg atg gcg atc agc      1056
Ala Trp Leu Val Asp Gly Arg Tyr Glu Thr Ile Ser Met Ala Ile Ser
        340                 345                 350 agt atg atc ggc gat gtc agc ggc atg att tgc gat ggt gcg tcg aac      1104
Ser Met Ile Gly Asp Val Ser Gly Met Ile Cys Asp Gly Ala Ser Asn
355                 360                 365 agc tgc gcg atg aag gtt tcg acc agt gct tcg gct gcg tgg aaa gcg      1152
Ser Cys Ala Met Lys Val Ser Thr Ser Ala Ser Ala Ala Trp Lys Ala
    370                 375                 380 gtg tta atg gcg ctg gat gat acc gcc gtg acc ggc aat gaa ggg att      1200
Val Leu Met Ala Leu Asp Asp Thr Ala Val Thr Gly Asn Glu Gly Ile
385                 390                 395                 400 gtg gcg cat gat gtt gag cag tcg att gcc aac ctg tgt gcg tta gca      1248
Val Ala His Asp Val Glu Gln Ser Ile Ala Asn Leu Cys Ala Leu Ala
            405                 410                 415 agc cat tcg atg cag caa acg gat cgg cag att atc gag att atg gcg      1296
Ser His Ser Met Gln Gln Thr Asp Arg Gln Ile Ile Glu Ile Met Ala
        420                 425                 430 agc aag gcc aga taa                                                  1311
Ser Lys Ala Arg
        435

<210> SEQ ID NO 2
<211> LENGTH: 436
<212> TYPE: PRT
<213> ORGANISM: Escherichia coli

<400> SEQUENCE: 2

Met Phe Asp Ser Thr Leu Asn Pro Leu Trp Gln Arg Tyr Ile Leu Ala
1               5                   10                  15

Val Gln Glu Glu Val Lys Pro Ala Leu Gly Cys Thr Glu Pro Ile Ser
                20                  25                  30

Leu Ala Leu Ala Ala Ala Val Ala Ala Glu Leu Glu Gly Pro Val
            35                  40                  45

Glu Arg Val Glu Ala Trp Val Ser Pro Asn Leu Met Lys Asn Gly Leu
    50                  55                  60

Gly Val Thr Val Pro Gly Thr Gly Met Val Gly Leu Pro Ile Ala Ala
65                  70                  75                  80

Ala Leu Gly Ala Leu Gly Gly Asn Ala Asn Ala Gly Leu Glu Val Leu
                85                  90                  95

Lys Asp Ala Thr Ala Gln Ala Ile Ala Asp Ala Lys Ala Leu Leu Ala
            100                 105                 110

Ala Gly Lys Val Ser Val Lys Ile Gln Glu Pro Cys Asp Glu Ile Leu
        115                 120                 125

Phe Ser Arg Ala Lys Val Trp Asn Gly Glu Lys Trp Ala Cys Val Thr
    130                 135                 140

Ile Val Gly Gly His Thr Asn Ile Val His Ile Glu Thr His Asp Gly
145                 150                 155                 160

Val Val Phe Thr Gln Gln Ala Cys Val Ala Glu Gly Glu Gln Glu Ser
                165                 170                 175

Pro Leu Thr Val Leu Ser Arg Thr Thr Leu Ala Glu Ile Leu Lys Phe
            180                 185                 190

Val Asn Glu Val Pro Phe Ala Ala Ile Arg Phe Ile Leu Asp Ser Ala
        195                 200                 205

Lys Leu Asn Cys Ala Leu Ser Gln Glu Gly Leu Ser Gly Lys Trp Gly
    210                 215                 220
```

Leu His Ile Gly Ala Thr Leu Glu Lys Gln Cys Glu Arg Gly Leu Leu
225                 230                 235                 240

Ala Lys Asp Leu Ser Ser Ile Val Ile Arg Thr Ser Ala Ala Ser
            245                 250                 255

Asp Ala Arg Met Gly Gly Ala Thr Leu Pro Ala Met Ser Asn Ser Gly
        260                 265                 270

Ser Gly Asn Gln Gly Ile Thr Ala Thr Met Pro Val Val Val Ala
    275                 280                 285

Glu His Phe Gly Ala Asp Asp Glu Arg Leu Ala Arg Ala Leu Met Leu
290                 295                 300

Ser His Leu Ser Ala Ile Tyr Ile His Asn Gln Leu Pro Arg Leu Ser
305                 310                 315                 320

Ala Leu Cys Ala Ala Thr Thr Ala Ala Met Gly Ala Ala Ala Gly Met
            325                 330                 335

Ala Trp Leu Val Asp Gly Arg Tyr Glu Thr Ile Ser Met Ala Ile Ser
        340                 345                 350

Ser Met Ile Gly Asp Val Ser Gly Met Ile Cys Asp Gly Ala Ser Asn
    355                 360                 365

Ser Cys Ala Met Lys Val Ser Thr Ser Ala Ser Ala Ala Trp Lys Ala
370                 375                 380

Val Leu Met Ala Leu Asp Asp Thr Ala Val Thr Gly Asn Glu Gly Ile
385                 390                 395                 400

Val Ala His Asp Val Glu Gln Ser Ile Ala Asn Leu Cys Ala Leu Ala
            405                 410                 415

Ser His Ser Met Gln Gln Thr Asp Arg Gln Ile Ile Glu Ile Met Ala
        420                 425                 430

Ser Lys Ala Arg
        435

<210> SEQ ID NO 3
<211> LENGTH: 34
<212> TYPE: DNA
<213> ORGANISM: Artificial
<220> FEATURE:
<223> OTHER INFORMATION: primer

<400> SEQUENCE: 3
cgcggatcca agatgcctgc cgagaagatt aacg                                  34

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
cgcggatccg agcgagctgg aagctatcg                                        29

<210> SEQ ID NO 5
<211> LENGTH: 80
<212> TYPE: DNA
<213> ORGANISM: Artificial
<220> FEATURE:
<223> OTHER INFORMATION: primer

<400> SEQUENCE: 5
atgtttgatt cgactttaaa tccgttatgg cagcgttaca tcctcgccgt tgaagcctgc     60
ttttttatac taagttggca                                                 80

<210> SEQ ID NO 6
<211> LENGTH: 80
<212> TYPE: DNA
<213> ORGANISM: Artificial
<220> FEATURE:
<223> OTHER INFORMATION: primer

<400> SEQUENCE: 6
ttatctggcc ttgctcgcca taatctcgat aatctgccga tccgtttgct cgctcaagtt    60
agtataaaaa agctgaacga                                                80

<210> SEQ ID NO 7
<211> LENGTH: 33
<212> TYPE: DNA
<213> ORGANISM: Artificial
<220> FEATURE:
<223> OTHER INFORMATION: primer

<400> SEQUENCE: 7
agctgagtcg acatgtcgtg tgaagaactg gaa                                  33

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8
agctgatcta gaatagatga ttacatcgca tcc                                  33

<210> SEQ ID NO 9
<211> LENGTH: 34
<212> TYPE: DNA
<213> ORGANISM: Artificial
<220> FEATURE:
<223> OTHER INFORMATION: primer

<400> SEQUENCE: 9
agctgagtcg acaaccctct gttatatgcc ttta                                 34

<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
agctgagcat gcgagtgaag gttttgtttt gac                                  33

<210> SEQ ID NO 11
<211> LENGTH: 62
<212> TYPE: DNA
<213> ORGANISM: Artificial
<220> FEATURE:
<223> OTHER INFORMATION: primer

<400> SEQUENCE: 11
aagcttaaca cagaaaaaag cccgcacctg acagtgcggg cttttttttt cgaccactgc    60
ag                                                                    62

<210> SEQ ID NO 12
<211> LENGTH: 62
<212> TYPE: DNA

<213> ORGANISM: Artificial
<220> FEATURE:
<223> OTHER INFORMATION: primer

<400> SEQUENCE: 12
ttcgaattgt gtcttttttc gggcgtggac tgtcacgccc gaaaaaaaaa gctggtgacg    60
tc                                                                  62

<210> SEQ ID NO 13
<211> LENGTH: 37
<212> TYPE: DNA
<213> ORGANISM: Artificial
<220> FEATURE:
<223> OTHER INFORMATION: primer

<400> SEQUENCE: 13
ccagatcttg aagcctgctt ttttatacta agttggc                             37

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
gaaatcaaat aatgatttta ttttg                                          25

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
ttacgccccg ccctgccact catcgc                                         26

<210> SEQ ID NO 16
<211> LENGTH: 34
<212> TYPE: DNA
<213> ORGANISM: Artificial
<220> FEATURE:
<223> OTHER INFORMATION: primer

<400> SEQUENCE: 16
gtcactgcag ctgatgtccg gcggtgcttt tgcc                                34

<210> SEQ ID NO 17
<211> LENGTH: 31
<212> TYPE: DNA
<213> ORGANISM: Artificial
<220> FEATURE:
<223> OTHER INFORMATION: primer

<400> SEQUENCE: 17
cagctgcagt ctgttacagg tcactaatac c                                   31

<210> SEQ ID NO 18
<211> LENGTH: 37
<212> TYPE: DNA
<213> ORGANISM: Artificial
<220> FEATURE:
<223> OTHER INFORMATION: primer

<400> SEQUENCE: 18

```
ccgagctccg ctcaagttag tataaaaaag ctgaacg                              37
```

<210> SEQ ID NO 19
<211> LENGTH: 70
<212> TYPE: DNA
<213> ORGANISM: Artificial
<220> FEATURE:
<223> OTHER INFORMATION: primer

<400> SEQUENCE: 19

```
cccgagctcg gtacctcgcg aatgcatcta gatgggcccg tcgactgcag aggcctgcat   60
gcaagcttcc                                                           70
```

<210> SEQ ID NO 20
<211> LENGTH: 1311
<212> TYPE: DNA
<213> ORGANISM: Shigella boydii
<220> FEATURE:
<221> NAME/KEY: CDS
<222> LOCATION: (1)..(1311)

<400> SEQUENCE: 20

| | | | | | | | | | | | | | | | |
|---|---|---|---|---|---|---|---|---|---|---|---|---|---|---|---|
| atg | ttt | gat | tcg | act | tta | aat | ccg | tta | tgg | cag | cgt | tac | atc | ctc | gcc | 48 |
| Met | Phe | Asp | Ser | Thr | Leu | Asn | Pro | Leu | Trp | Gln | Arg | Tyr | Ile | Leu | Ala | |
| 1 | | | | 5 | | | | | 10 | | | | | 15 | | |

```
gtt cag gag gaa gta aaa ccg gcg ctg gga tgt act gaa ccg att tca     96
Val Gln Glu Glu Val Lys Pro Ala Leu Gly Cys Thr Glu Pro Ile Ser
             20                  25                  30 ctg gcg ctg gcg gcg gcg gtt gct gcg gca gaa ctg gaa ggt ccg gtt    144
Leu Ala Leu Ala Ala Ala Val Ala Ala Ala Glu Leu Glu Gly Pro Val
         35                  40                  45 gaa cgt gta gaa gcc tgg gtt tcg cca aat ctg atg aag aac ggt ctg    192
Glu Arg Val Glu Ala Trp Val Ser Pro Asn Leu Met Lys Asn Gly Leu
     50                  55                  60 ggc gtc acc gtt ccc ggc acg gga atg gtg ggg ctg ccg att gcg gcg    240
Gly Val Thr Val Pro Gly Thr Gly Met Val Gly Leu Pro Ile Ala Ala
 65                  70                  75                  80 gcg ctg ggg gcg tta ggt gga aat gcc aac gcc ggg ctg gaa gtg ctg    288
Ala Leu Gly Ala Leu Gly Gly Asn Ala Asn Ala Gly Leu Glu Val Leu
                 85                  90                  95 aaa gac gca act gcg cag gca att gcc gat gcc aaa gca ctg ctg gcg    336
Lys Asp Ala Thr Ala Gln Ala Ile Ala Asp Ala Lys Ala Leu Leu Ala
            100                 105                 110 gcg ggg aaa gtc tcc gtt aag atc cag gaa cct tgc aat gaa atc ctc    384
Ala Gly Lys Val Ser Val Lys Ile Gln Glu Pro Cys Asn Glu Ile Leu
        115                 120                 125 ttc tca cgc gcc aaa gtc tgg aac ggt gag aag tgg gcg tgt gtc acc    432
Phe Ser Arg Ala Lys Val Trp Asn Gly Glu Lys Trp Ala Cys Val Thr
    130                 135                 140 atc gtc ggc ggg cat acc aac att gtg cat att gag acg cac aat agt    480
Ile Val Gly Gly His Thr Asn Ile Val His Ile Glu Thr His Asn Ser
145                 150                 155                 160 gtg gtg ttt acc cag cag gcg tgt gtg gca gag ggc gag caa gag tct    528
Val Val Phe Thr Gln Gln Ala Cys Val Ala Glu Gly Glu Gln Glu Ser
                165                 170                 175 ccg ctg acg gtg ctt tcc aga acg acg ctg gct gag atc ctg aag ttc    576
Pro Leu Thr Val Leu Ser Arg Thr Thr Leu Ala Glu Ile Leu Lys Phe
            180                 185                 190 gtc aat gaa gtc ccg ttt gcg gcg atc cgc ttt att ctc gat tcc gcg    624
Val Asn Glu Val Pro Phe Ala Ala Ile Arg Phe Ile Leu Asp Ser Ala
        195                 200                 205 aag cta aat tgt gcg tta tcg cag gaa ggt ttg agc ggt aag tgg ggg    672
Lys Leu Asn Cys Ala Leu Ser Gln Glu Gly Leu Ser Gly Lys Trp Gly
```

```
              Lys Leu Asn Cys Ala Leu Ser Gln Glu Gly Leu Ser Gly Lys Trp Gly
                  210                 215                 220 ctg cat att ggc gcg acg ctg gaa aaa cag tgc gag cgc ggt ttg ctg       720
Leu His Ile Gly Ala Thr Leu Glu Lys Gln Cys Glu Arg Gly Leu Leu
225                 230                 235                 240 gcg aaa gat ctc tct tca tcc att gtg att cgt acc agc gcg gca tcc       768
Ala Lys Asp Leu Ser Ser Ser Ile Val Ile Arg Thr Ser Ala Ala Ser
                245                 250                 255 gat gcg cgt atg ggc ggc gct acg ctt ccg gct atg agt aac tcc ggc       816
Asp Ala Arg Met Gly Gly Ala Thr Leu Pro Ala Met Ser Asn Ser Gly
            260                 265                 270 tcg ggt aac cag ggg atc acc gca aca atg cct gtg gtg gtt gta gca       864
Ser Gly Asn Gln Gly Ile Thr Ala Thr Met Pro Val Val Val Val Ala
        275                 280                 285 gaa cac ttc gga gcg gat gat gaa cga ctg gcg cgt gcg ctg atg ctt       912
Glu His Phe Gly Ala Asp Asp Glu Arg Leu Ala Arg Ala Leu Met Leu
    290                 295                 300 tct cat ttg agc gca att tac atc cat aac cag tta ccg cgt ttg tct       960
Ser His Leu Ser Ala Ile Tyr Ile His Asn Gln Leu Pro Arg Leu Ser
305                 310                 315                 320 gca ctt tgt gcc gca acg acc gca gca atg ggg gcc gcc gcg ggg atg      1008
Ala Leu Cys Ala Ala Thr Thr Ala Ala Met Gly Ala Ala Ala Gly Met
                325                 330                 335 gca tgg ctg gtg gat ggg cgt tat gaa act atc tcg atg gcg atc agc      1056
Ala Trp Leu Val Asp Gly Arg Tyr Glu Thr Ile Ser Met Ala Ile Ser
            340                 345                 350 agt atg atc ggc gat gtc agc ggc atg att tgc gat ggt gcg tcg aac      1104
Ser Met Ile Gly Asp Val Ser Gly Met Ile Cys Asp Gly Ala Ser Asn
        355                 360                 365 agc tgc gcg atg aag gtt tcg acc agt gct tcg gct gcg tgg aaa gcg      1152
Ser Cys Ala Met Lys Val Ser Thr Ser Ala Ser Ala Ala Trp Lys Ala
    370                 375                 380 gtg tta atg gcg ctg gat gat acc gcc gtg acc ggc aat gaa ggg atc      1200
Val Leu Met Ala Leu Asp Asp Thr Ala Val Thr Gly Asn Glu Gly Ile
385                 390                 395                 400 gtg gcg cat gat gtt gag cag tcg att gcc aac ctg tgt gcg tta gca      1248
Val Ala His Asp Val Glu Gln Ser Ile Ala Asn Leu Cys Ala Leu Ala
                405                 410                 415 agc cat tcg atg cag caa acg gat cgg cag att atc gag att atg gcg      1296
Ser His Ser Met Gln Gln Thr Asp Arg Gln Ile Ile Glu Ile Met Ala
            420                 425                 430 agc aag gcc aga taa                                                  1311
Ser Lys Ala Arg
        435

<210> SEQ ID NO 21
<211> LENGTH: 436
<212> TYPE: PRT
<213> ORGANISM: Shigella boydii

<400> SEQUENCE: 21

Met Phe Asp Ser Thr Leu Asn Pro Leu Trp Gln Arg Tyr Ile Leu Ala
1               5                   10                  15

Val Gln Glu Glu Val Lys Pro Ala Leu Gly Cys Thr Glu Pro Ile Ser
                20                  25                  30

Leu Ala Leu Ala Ala Ala Val Ala Ala Ala Glu Leu Glu Gly Pro Val
            35                  40                  45

Glu Arg Val Glu Ala Trp Val Ser Pro Asn Leu Met Lys Asn Gly Leu
        50                  55                  60

Gly Val Thr Val Pro Gly Thr Gly Met Val Gly Leu Pro Ile Ala Ala
```

```
            65                   70                  75                  80
Ala Leu Gly Ala Leu Gly Gly Asn Ala Asn Ala Gly Leu Glu Val Leu
                    85                  90                  95

Lys Asp Ala Thr Ala Gln Ala Ile Ala Asp Ala Lys Ala Leu Leu Ala
            100                 105                 110

Ala Gly Lys Val Ser Val Lys Ile Gln Glu Pro Cys Asn Glu Ile Leu
            115                 120                 125

Phe Ser Arg Ala Lys Val Trp Asn Gly Glu Lys Trp Ala Cys Val Thr
        130                 135                 140

Ile Val Gly Gly His Thr Asn Ile Val His Ile Glu Thr His Asn Ser
145                 150                 155                 160

Val Val Phe Thr Gln Gln Ala Cys Val Ala Glu Gly Glu Gln Glu Ser
                165                 170                 175

Pro Leu Thr Val Leu Ser Arg Thr Thr Leu Ala Glu Ile Leu Lys Phe
            180                 185                 190

Val Asn Glu Val Pro Phe Ala Ala Ile Arg Phe Ile Leu Asp Ser Ala
            195                 200                 205

Lys Leu Asn Cys Ala Leu Ser Gln Glu Gly Leu Ser Gly Lys Trp Gly
        210                 215                 220

Leu His Ile Gly Ala Thr Leu Glu Lys Gln Cys Glu Arg Gly Leu Leu
225                 230                 235                 240

Ala Lys Asp Leu Ser Ser Ile Val Ile Arg Thr Ser Ala Ala Ser
                245                 250                 255

Asp Ala Arg Met Gly Gly Ala Thr Leu Pro Ala Met Ser Asn Ser Gly
            260                 265                 270

Ser Gly Asn Gln Gly Ile Thr Ala Thr Met Pro Val Val Val Ala
            275                 280                 285

Glu His Phe Gly Ala Asp Asp Glu Arg Leu Ala Arg Ala Leu Met Leu
        290                 295                 300

Ser His Leu Ser Ala Ile Tyr Ile His Asn Gln Leu Pro Arg Leu Ser
305                 310                 315                 320

Ala Leu Cys Ala Ala Thr Thr Ala Ala Met Gly Ala Ala Ala Gly Met
                325                 330                 335

Ala Trp Leu Val Asp Gly Arg Tyr Glu Thr Ile Ser Met Ala Ile Ser
            340                 345                 350

Ser Met Ile Gly Asp Val Ser Gly Met Ile Cys Asp Gly Ala Ser Asn
            355                 360                 365

Ser Cys Ala Met Lys Val Ser Thr Ser Ala Ser Ala Trp Lys Ala
        370                 375                 380

Val Leu Met Ala Leu Asp Asp Thr Ala Val Thr Gly Asn Glu Gly Ile
385                 390                 395                 400

Val Ala His Asp Val Glu Gln Ser Ile Ala Asn Leu Cys Ala Leu Ala
                405                 410                 415

Ser His Ser Met Gln Gln Thr Asp Arg Gln Ile Ile Glu Ile Met Ala
            420                 425                 430

Ser Lys Ala Arg
        435

<210> SEQ ID NO 22
<211> LENGTH: 1311
<212> TYPE: DNA
<213> ORGANISM: Citrobacter koseri
<220> FEATURE:
<221> NAME/KEY: CDS
<222> LOCATION: (1)..(1311)
```

<400> SEQUENCE: 22

```
atg ttt gag tct aca gaa aat ccg tta tgg cag cgt ttt atc ctc gca      48
Met Phe Glu Ser Thr Glu Asn Pro Leu Trp Gln Arg Phe Ile Leu Ala
1               5                   10                  15 gta cag gaa gag gta aaa ccg gca ctg gga tgt acg gaa cct gtc tct      96
Val Gln Glu Glu Val Lys Pro Ala Leu Gly Cys Thr Glu Pro Val Ser
                20                  25                  30 ctg gcg ctg gcg gcg gcg gtt gcc gcg gct gaa ctt gac ggc gaa gtt     144
Leu Ala Leu Ala Ala Ala Val Ala Ala Glu Leu Asp Gly Glu Val
            35                  40                  45 gaa cgc gtt gac gcg tgg gtc tcg ccg aac ctg atg aag aat ggc ctg     192
Glu Arg Val Asp Ala Trp Val Ser Pro Asn Leu Met Lys Asn Gly Leu
        50                  55                  60 ggc gtc acc gta ccg ggc acc ggg atg gtt ggg ctt ccc att gcg gca     240
Gly Val Thr Val Pro Gly Thr Gly Met Val Gly Leu Pro Ile Ala Ala
65                  70                  75                  80 gcg ctg ggg gcg ctt ggc ggc gat gcc agc gcg ggg ctg gaa gtg ttg     288
Ala Leu Gly Ala Leu Gly Gly Asp Ala Ser Ala Gly Leu Glu Val Leu
                85                  90                  95 aaa aac gcc tct tcg ggg gcg att gcg gat gcg aaa gcg atg ctg gct     336
Lys Asn Ala Ser Ser Gly Ala Ile Ala Asp Ala Lys Ala Met Leu Ala
                100                 105                 110 gcc ggg aag gtg tcg gtg atg ttg cag gag cca tgc gac gac atc ctc     384
Ala Gly Lys Val Ser Val Met Leu Gln Glu Pro Cys Asp Asp Ile Leu
            115                 120                 125 ttc tca cgc gct aaa gtg tac agc ggc gat gcg tgg gcc tgc gta acg     432
Phe Ser Arg Ala Lys Val Tyr Ser Gly Asp Ala Trp Ala Cys Val Thr
        130                 135                 140 atc gtc ggc ggg cac acc aat atc gtg cgc att gaa act cac act ggg     480
Ile Val Gly Gly His Thr Asn Ile Val Arg Ile Glu Thr His Thr Gly
145                 150                 155                 160 gtg atc ttt acg cag acc gaa agc gtg cag ggg gag gcg caa gaa tcg     528
Val Ile Phe Thr Gln Thr Glu Ser Val Gln Gly Glu Ala Gln Glu Ser
                165                 170                 175 ccg ctg tcg gtc tta tca aag acc tcg ctg gaa gag att ctg gcg ttt     576
Pro Leu Ser Val Leu Ser Lys Thr Ser Leu Glu Glu Ile Leu Ala Phe
            180                 185                 190 gtg aat gcg gtg cca ttt gtg tca atc cgc ttt att ctg gag gcc gcc     624
Val Asn Ala Val Pro Phe Val Ser Ile Arg Phe Ile Leu Glu Ala Ala
        195                 200                 205 aga ctg aac ggc gcg ctg tcg cag gaa gga ttg cgc ggc acc tgg ggg     672
Arg Leu Asn Gly Ala Leu Ser Gln Glu Gly Leu Arg Gly Thr Trp Gly
    210                 215                 220 ctg cat atc ggg gcg acg ttg caa aag cag tgc gca cgc ggt ctg ctg     720
Leu His Ile Gly Ala Thr Leu Gln Lys Gln Cys Ala Arg Gly Leu Leu
225                 230                 235                 240 gcg gac gat ctg tca acg gcg atc ctg att cgc acc agc gca gct tcg     768
Ala Asp Asp Leu Ser Thr Ala Ile Leu Ile Arg Thr Ser Ala Ala Ser
                245                 250                 255 gat gcg cgg atg ggc ggc gcg acg ctg cca gcc atg agt aac tcc ggc     816
Asp Ala Arg Met Gly Gly Ala Thr Leu Pro Ala Met Ser Asn Ser Gly
            260                 265                 270 tcc ggc aat cag ggg atc acc gcg acg gtt ccc gta atg gtg gtg gcg     864
Ser Gly Asn Gln Gly Ile Thr Ala Thr Val Pro Val Met Val Val Ala
        275                 280                 285 gag cat gtg ggg gcg gat gac gaa cgt ctg gcg cgc gcc ctg atg ctc     912
Glu His Val Gly Ala Asp Asp Glu Arg Leu Ala Arg Ala Leu Met Leu
    290                 295                 300 tcg cac ctg agc gcg atc tac att cac cat cag ctt cca cgc ctg tca     960
Ser His Leu Ser Ala Ile Tyr Ile His His Gln Leu Pro Arg Leu Ser
```

```
                305                 310                 315                 320
gcg ctc tgt gcg gcg acc acg gcg gca atg ggg gcg gcg gga atg            1008
Ala Leu Cys Ala Ala Thr Thr Ala Ala Met Gly Ala Ala Gly Met
                325                 330                 335 gcg tgg ctg atg gat ggc cgc tat aac acg att gcg atg gcg atc agc        1056
Ala Trp Leu Met Asp Gly Arg Tyr Asn Thr Ile Ala Met Ala Ile Ser
            340                 345                 350 agt atg atc ggc gac gtg agc ggg atg ata tgc gac ggc gca tcg aat        1104
Ser Met Ile Gly Asp Val Ser Gly Met Ile Cys Asp Gly Ala Ser Asn
        355                 360                 365 agc tgt gcg atg aag gta tcg acc agc gcg tct gcg gcc tgg aaa gcg        1152
Ser Cys Ala Met Lys Val Ser Thr Ser Ala Ser Ala Ala Trp Lys Ala
    370                 375                 380 gtg tta atg gcg ctg gat gat acg gcg gtg acc ggc aac gaa gga att        1200
Val Leu Met Ala Leu Asp Asp Thr Ala Val Thr Gly Asn Glu Gly Ile
385                 390                 395                 400 gtg gcg cat aac gtc gag caa tct att tcg aat tta tgc gcg ttg gcc        1248
Val Ala His Asn Val Glu Gln Ser Ile Ser Asn Leu Cys Ala Leu Ala
                405                 410                 415 tgt cat gca atg cag caa acc gac cgt cag gtt atc gaa att atg gcc        1296
Cys His Ala Met Gln Gln Thr Asp Arg Gln Val Ile Glu Ile Met Ala
            420                 425                 430 agt aag gcg cat taa                                                    1311
Ser Lys Ala His
        435

<210> SEQ ID NO 23
<211> LENGTH: 436
<212> TYPE: PRT
<213> ORGANISM: Citrobacter koseri

<400> SEQUENCE: 23

Met Phe Glu Ser Thr Glu Asn Pro Leu Trp Gln Arg Phe Ile Leu Ala
1               5                   10                  15

Val Gln Glu Glu Val Lys Pro Ala Leu Gly Cys Thr Glu Pro Val Ser
                20                  25                  30

Leu Ala Leu Ala Ala Ala Val Ala Ala Glu Leu Asp Gly Glu Val
            35                  40                  45

Glu Arg Val Asp Ala Trp Val Ser Pro Asn Leu Met Lys Asn Gly Leu
    50                  55                  60

Gly Val Thr Val Pro Gly Thr Gly Met Val Gly Leu Pro Ile Ala Ala
65                  70                  75                  80

Ala Leu Gly Ala Leu Gly Gly Asp Ala Ser Ala Gly Leu Glu Val Leu
                85                  90                  95

Lys Asn Ala Ser Ser Gly Ala Ile Ala Asp Ala Lys Ala Met Leu Ala
            100                 105                 110

Ala Gly Lys Val Ser Val Met Leu Gln Glu Pro Cys Asp Asp Ile Leu
        115                 120                 125

Phe Ser Arg Ala Lys Val Tyr Ser Gly Asp Ala Trp Ala Cys Val Thr
    130                 135                 140

Ile Val Gly Gly His Thr Asn Ile Val Arg Ile Glu Thr His Thr Gly
145                 150                 155                 160

Val Ile Phe Thr Gln Thr Glu Ser Val Gln Gly Glu Ala Gln Glu Ser
                165                 170                 175

Pro Leu Ser Val Leu Ser Lys Thr Ser Leu Glu Glu Ile Leu Ala Phe
            180                 185                 190

Val Asn Ala Val Pro Phe Val Ser Ile Arg Phe Ile Leu Glu Ala Ala
        195                 200                 205
```

Arg Leu Asn Gly Ala Leu Ser Gln Glu Gly Leu Arg Gly Thr Trp Gly
    210                 215                 220

Leu His Ile Gly Ala Thr Leu Gln Lys Gln Cys Ala Arg Gly Leu Leu
225                 230                 235                 240

Ala Asp Asp Leu Ser Thr Ala Ile Leu Ile Arg Thr Ser Ala Ala Ser
                245                 250                 255

Asp Ala Arg Met Gly Gly Ala Thr Leu Pro Ala Met Ser Asn Ser Gly
            260                 265                 270

Ser Gly Asn Gln Gly Ile Thr Ala Thr Val Pro Val Met Val Val Ala
        275                 280                 285

Glu His Val Gly Ala Asp Asp Glu Arg Leu Ala Arg Ala Leu Met Leu
    290                 295                 300

Ser His Leu Ser Ala Ile Tyr Ile His His Gln Leu Pro Arg Leu Ser
305                 310                 315                 320

Ala Leu Cys Ala Ala Thr Thr Ala Ala Met Gly Ala Ala Ala Gly Met
                325                 330                 335

Ala Trp Leu Met Asp Gly Arg Tyr Asn Thr Ile Ala Met Ala Ile Ser
            340                 345                 350

Ser Met Ile Gly Asp Val Ser Gly Met Ile Cys Asp Gly Ala Ser Asn
        355                 360                 365

Ser Cys Ala Met Lys Val Ser Thr Ser Ala Ser Ala Ala Trp Lys Ala
    370                 375                 380

Val Leu Met Ala Leu Asp Asp Thr Ala Val Thr Gly Asn Glu Gly Ile
385                 390                 395                 400

Val Ala His Asn Val Glu Gln Ser Ile Ser Asn Leu Cys Ala Leu Ala
                405                 410                 415

Cys His Ala Met Gln Gln Thr Asp Arg Gln Val Ile Glu Ile Met Ala
            420                 425                 430

Ser Lys Ala His
        435

<210> SEQ ID NO 24
<211> LENGTH: 1311
<212> TYPE: DNA
<213> ORGANISM: Salmonella typhimurium
<220> FEATURE:
<221> NAME/KEY: CDS
<222> LOCATION: (1)..(1311)

<400> SEQUENCE: 24 atg ttt gaa tct aaa ata aat cca ttg tgg caa agt ttt att ctg gcc    48
Met Phe Glu Ser Lys Ile Asn Pro Leu Trp Gln Ser Phe Ile Leu Ala
1               5                   10                  15 gta cag gaa gaa gta aaa ccg gcg ctg ggg tgt act gag cca att tca    96
Val Gln Glu Glu Val Lys Pro Ala Leu Gly Cys Thr Glu Pro Ile Ser
            20                  25                  30 ctg gcg ctg gcg gca gcg gcg gcg gcg gct gaa ctt aac ggc aca gtt   144
Leu Ala Leu Ala Ala Ala Ala Ala Ala Ala Glu Leu Asn Gly Thr Val
        35                  40                  45 gaa cgc att gac gcg tgg gtt tcg ccc aat ctg atg aaa aat ggt atg   192
Glu Arg Ile Asp Ala Trp Val Ser Pro Asn Leu Met Lys Asn Gly Met
    50                  55                  60 ggc gtt acc gtt cca gga acg gga atg gta ggg cta ccg atc gcc gcg   240
Gly Val Thr Val Pro Gly Thr Gly Met Val Gly Leu Pro Ile Ala Ala
65                  70                  75                  80 gcg ttg ggc gcg ttg ggc ggt gat gcg aaa gcc ggg ttg gag gtg tta   288
Ala Leu Gly Ala Leu Gly Gly Asp Ala Lys Ala Gly Leu Glu Val Leu
                85                  90                  95

| | | | | | | | | | | | | | | | | |
|---|---|---|---|---|---|---|---|---|---|---|---|---|---|---|---|---|
| aaa | gac | gct | tcc | gct | aaa | gcc | gtt | gcc | gat | gca | aaa | gcg | atg | ctg | gcc | 336 |
| Lys | Asp | Ala | Ser | Ala | Lys | Ala | Val | Ala | Asp | Ala | Lys | Ala | Met | Leu | Ala | |
| | | | 100 | | | | 105 | | | | 110 | | | | | |
| gct | gga | cat | gtc | gcg | gtg | atg | ttg | cag | gag | cca | tgt | aac | gat | att | ctg | 384 |
| Ala | Gly | His | Val | Ala | Val | Met | Leu | Gln | Glu | Pro | Cys | Asn | Asp | Ile | Leu | |
| | | 115 | | | | 120 | | | | 125 | | | | | | |
| ttt | tca | cgg | gcg | aaa | gtg | tat | agc | ggc | gat | agc | tgg | gca | tgt | gtc | acg | 432 |
| Phe | Ser | Arg | Ala | Lys | Val | Tyr | Ser | Gly | Asp | Ser | Trp | Ala | Cys | Val | Thr | |
| | 130 | | | | | 135 | | | | | 140 | | | | | |
| atc | gtc | ggc | gat | cat | aca | aat | att | gtg | cgg | ata | gaa | acc | gac | aag | ggt | 480 |
| Ile | Val | Gly | Asp | His | Thr | Asn | Ile | Val | Arg | Ile | Glu | Thr | Asp | Lys | Gly | |
| 145 | | | | | 150 | | | | | 155 | | | | | 160 | |
| gtg | gta | ttt | acc | cag | gcc | gat | aat | gcg | cag | gaa | gaa | gaa | aaa | acc | tcg | 528 |
| Val | Val | Phe | Thr | Gln | Ala | Asp | Asn | Ala | Gln | Glu | Glu | Glu | Lys | Thr | Ser | |
| | | | | 165 | | | | | 170 | | | | | 175 | | |
| cca | ctg | gga | gtg | ctg | tct | cat | acc | tcg | ctg | gaa | gag | atc | ctg | gcg | ttt | 576 |
| Pro | Leu | Gly | Val | Leu | Ser | His | Thr | Ser | Leu | Glu | Glu | Ile | Leu | Ala | Phe | |
| | | | 180 | | | | | 185 | | | | | 190 | | | |
| gtg | aat | gcg | gtg | ccc | ttt | gac | gct | atc | cgc | ttt | att | ctc | gat | gcg | gcc | 624 |
| Val | Asn | Ala | Val | Pro | Phe | Asp | Ala | Ile | Arg | Phe | Ile | Leu | Asp | Ala | Ala | |
| | | 195 | | | | | 200 | | | | | 205 | | | | |
| agg | cta | aac | ggc | gcg | ttg | tcg | cag | gag | gga | ctg | cgt | ggt | tcc | tgg | ggg | 672 |
| Arg | Leu | Asn | Gly | Ala | Leu | Ser | Gln | Glu | Gly | Leu | Arg | Gly | Ser | Trp | Gly | |
| | 210 | | | | | 215 | | | | | 220 | | | | | |
| ctg | cat | atc | ggt | tcg | acg | ctg | gcc | aaa | cag | tgc | gat | cgc | ggt | ctg | ctg | 720 |
| Leu | His | Ile | Gly | Ser | Thr | Leu | Ala | Lys | Gln | Cys | Asp | Arg | Gly | Leu | Leu | |
| 225 | | | | | 230 | | | | | 235 | | | | | 240 | |
| gcg | aaa | gat | ctc | tcc | acg | gcg | att | ttg | atc | cgt | acc | agc | gcg | gcg | tca | 768 |
| Ala | Lys | Asp | Leu | Ser | Thr | Ala | Ile | Leu | Ile | Arg | Thr | Ser | Ala | Ala | Ser | |
| | | | | 245 | | | | | 250 | | | | | 255 | | |
| gac | gcc | aga | atg | ggc | ggt | gcc | acg | ttg | ccc | gcg | atg | agc | aac | tcc | ggc | 816 |
| Asp | Ala | Arg | Met | Gly | Gly | Ala | Thr | Leu | Pro | Ala | Met | Ser | Asn | Ser | Gly | |
| | | | 260 | | | | | 265 | | | | | 270 | | | |
| tcc | ggc | aac | cag | ggg | att | acc | gcc | acg | gtg | cca | gtc | atg | gtg | gtt | gct | 864 |
| Ser | Gly | Asn | Gln | Gly | Ile | Thr | Ala | Thr | Val | Pro | Val | Met | Val | Val | Ala | |
| | | 275 | | | | | 280 | | | | | 285 | | | | |
| gaa | cat | gtc | ggc | gcc | gat | gac | gag | cgc | ctg | gcg | cgc | gcg | cta | atg | tta | 912 |
| Glu | His | Val | Gly | Ala | Asp | Asp | Glu | Arg | Leu | Ala | Arg | Ala | Leu | Met | Leu | |
| | 290 | | | | | 295 | | | | | 300 | | | | | |
| tcg | cat | ttg | agc | gct | atc | tat | att | cac | cat | cag | ctt | ccg | cgt | ttg | tcg | 960 |
| Ser | His | Leu | Ser | Ala | Ile | Tyr | Ile | His | His | Gln | Leu | Pro | Arg | Leu | Ser | |
| 305 | | | | | 310 | | | | | 315 | | | | | 320 | |
| gcg | ctg | tgc | gcg | gca | act | acg | gcg | gcg | atg | ggc | gcg | gca | gcg | ggt | atg | 1008 |
| Ala | Leu | Cys | Ala | Ala | Thr | Thr | Ala | Ala | Met | Gly | Ala | Ala | Ala | Gly | Met | |
| | | | | 325 | | | | | 330 | | | | | 335 | | |
| gcg | tgg | ctg | ata | gat | ggt | cgt | tac | gac | act | atc | gca | atg | gct | atc | agc | 1056 |
| Ala | Trp | Leu | Ile | Asp | Gly | Arg | Tyr | Asp | Thr | Ile | Ala | Met | Ala | Ile | Ser | |
| | | | 340 | | | | | 345 | | | | | 350 | | | |
| agt | atg | att | ggt | gat | gtc | agc | ggg | atg | att | tgc | gat | ggc | gcg | tcg | aat | 1104 |
| Ser | Met | Ile | Gly | Asp | Val | Ser | Gly | Met | Ile | Cys | Asp | Gly | Ala | Ser | Asn | |
| | | 355 | | | | | 360 | | | | | 365 | | | | |
| agc | tgc | gcg | atg | aaa | gtc | tct | acc | agc | gcg | tcg | gcg | tgg | aaa | gcc | | 1152 |
| Ser | Cys | Ala | Met | Lys | Val | Ser | Thr | Ser | Ala | Ser | Ala | Trp | Lys | Ala | | |
| | 370 | | | | | 375 | | | | | 380 | | | | | |
| gta | ctg | atg | gcg | ttg | gat | gat | acg | gcg | gtg | acc | gga | aac | gaa | ggg | att | 1200 |
| Val | Leu | Met | Ala | Leu | Asp | Asp | Thr | Ala | Val | Thr | Gly | Asn | Glu | Gly | Ile | |
| 385 | | | | | 390 | | | | | 395 | | | | | 400 | |
| gtg | gcg | cac | aat | gtc | gaa | caa | tct | att | tcg | aat | ttg | tgt | tcg | ctg | gcg | 1248 |
| Val | Ala | His | Asn | Val | Glu | Gln | Ser | Ile | Ser | Asn | Leu | Cys | Ser | Leu | Ala | |
| | | | | 405 | | | | | 410 | | | | | 415 | | |

```
tgt cgc tca atg cag cag acc gac aag cag atc atc gag att atg gcc   1296
Cys Arg Ser Met Gln Gln Thr Asp Lys Gln Ile Ile Glu Ile Met Ala
            420                 425                 430 agt aaa gcg cat taa                                               1311
Ser Lys Ala His
        435

<210> SEQ ID NO 25
<211> LENGTH: 436
<212> TYPE: PRT
<213> ORGANISM: Salmonella typhimurium

<400> SEQUENCE: 25

Met Phe Glu Ser Lys Ile Asn Pro Leu Trp Gln Ser Phe Ile Leu Ala
1               5                   10                  15

Val Gln Glu Glu Val Lys Pro Ala Leu Gly Cys Thr Glu Pro Ile Ser
            20                  25                  30

Leu Ala Leu Ala Ala Ala Ala Ala Ala Glu Leu Asn Gly Thr Val
        35                  40                  45

Glu Arg Ile Asp Ala Trp Val Ser Pro Asn Leu Met Lys Asn Gly Met
    50                  55                  60

Gly Val Thr Val Pro Gly Thr Gly Met Val Gly Leu Pro Ile Ala Ala
65                  70                  75                  80

Ala Leu Gly Ala Leu Gly Gly Asp Ala Lys Ala Gly Leu Glu Val Leu
                85                  90                  95

Lys Asp Ala Ser Ala Lys Ala Val Ala Asp Ala Lys Ala Met Leu Ala
            100                 105                 110

Ala Gly His Val Ala Val Met Leu Gln Glu Pro Cys Asn Asp Ile Leu
        115                 120                 125

Phe Ser Arg Ala Lys Val Tyr Ser Gly Asp Ser Trp Ala Cys Val Thr
    130                 135                 140

Ile Val Gly Asp His Thr Asn Ile Val Arg Ile Glu Thr Asp Lys Gly
145                 150                 155                 160

Val Val Phe Thr Gln Ala Asp Asn Ala Gln Glu Glu Lys Thr Ser
                165                 170                 175

Pro Leu Gly Val Leu Ser His Thr Ser Leu Glu Glu Ile Leu Ala Phe
            180                 185                 190

Val Asn Ala Val Pro Phe Asp Ala Ile Arg Phe Ile Leu Asp Ala Ala
        195                 200                 205

Arg Leu Asn Gly Ala Leu Ser Gln Glu Gly Leu Arg Gly Ser Trp Gly
    210                 215                 220

Leu His Ile Gly Ser Thr Leu Ala Lys Gln Cys Asp Arg Gly Leu Leu
225                 230                 235                 240

Ala Lys Asp Leu Ser Thr Ala Ile Leu Ile Arg Thr Ser Ala Ala Ser
                245                 250                 255

Asp Ala Arg Met Gly Gly Ala Thr Leu Pro Ala Met Ser Asn Ser Gly
            260                 265                 270

Ser Gly Asn Gln Gly Ile Thr Ala Thr Val Pro Val Met Val Val Ala
        275                 280                 285

Glu His Val Gly Ala Asp Asp Glu Arg Leu Ala Arg Ala Leu Met Leu
    290                 295                 300

Ser His Leu Ser Ala Ile Tyr Ile His His Gln Leu Pro Arg Leu Ser
305                 310                 315                 320

Ala Leu Cys Ala Ala Thr Thr Ala Ala Met Gly Ala Ala Gly Met
                325                 330                 335
```

```
Ala Trp Leu Ile Asp Gly Arg Tyr Asp Thr Ile Ala Met Ala Ile Ser
            340                 345                 350

Ser Met Ile Gly Asp Val Ser Gly Met Ile Cys Asp Gly Ala Ser Asn
            355                 360                 365

Ser Cys Ala Met Lys Val Ser Thr Ser Ala Ser Ala Ala Trp Lys Ala
        370                 375                 380

Val Leu Met Ala Leu Asp Asp Thr Ala Val Thr Gly Asn Glu Gly Ile
385                 390                 395                 400

Val Ala His Asn Val Glu Gln Ser Ile Ser Asn Leu Cys Ser Leu Ala
                405                 410                 415

Cys Arg Ser Met Gln Gln Thr Asp Lys Gln Ile Glu Ile Met Ala
            420                 425                 430

Ser Lys Ala His
        435

<210> SEQ ID NO 26
<211> LENGTH: 1299
<212> TYPE: DNA
<213> ORGANISM: Actinobacillus pleuropneumoniae
<220> FEATURE:
<221> NAME/KEY: CDS
<222> LOCATION: (1)..(1299)

<400> SEQUENCE: 26 atg aag ttt aaa tcg gaa tta gaa caa gcg att att gcc acc gta caa      48
Met Lys Phe Lys Ser Glu Leu Glu Gln Ala Ile Ile Ala Thr Val Gln
1               5                   10                  15 caa gaa gtt gta ccg gca ctg ggt tgt acc gag cct gtt tct ttg gcg      96
Gln Glu Val Val Pro Ala Leu Gly Cys Thr Glu Pro Val Ser Leu Ala
                20                  25                  30 tta gca gcg gcg gtt gct cgt caa tat tta ggc gca tta ccg gat cgg     144
Leu Ala Ala Ala Val Ala Arg Gln Tyr Leu Gly Ala Leu Pro Asp Arg
            35                  40                  45 atc gag gct aaa gta tcg ccg aat tta atg aaa aac ggt atg ggg gta     192
Ile Glu Ala Lys Val Ser Pro Asn Leu Met Lys Asn Gly Met Gly Val
        50                  55                  60 acc gta ccc ggt acg gga acg gta gga cta act atg gcg gcg gca atc     240
Thr Val Pro Gly Thr Gly Thr Val Gly Leu Thr Met Ala Ala Ala Ile
65                  70                  75                  80 gga gcg att ggt ggc gat ccg aac ggc gga ttg gaa gtg ctt aaa cat     288
Gly Ala Ile Gly Gly Asp Pro Asn Gly Gly Leu Glu Val Leu Lys His
                85                  90                  95 att act aac gag caa gtg gca caa gcg aaa caa atg att cac gat cac     336
Ile Thr Asn Glu Gln Val Ala Gln Ala Lys Gln Met Ile His Asp His
                100                 105                 110 aaa atc gaa gtc agt att tcc gat acc gaa cat att ctc tat tcc gaa     384
Lys Ile Glu Val Ser Ile Ser Asp Thr Glu His Ile Leu Tyr Ser Glu
            115                 120                 125 gcc aca ctg ttt aat gcc gat cag caa gtg aaa gta cgt atc gcc gct     432
Ala Thr Leu Phe Asn Ala Asp Gln Gln Val Lys Val Arg Ile Ala Ala
        130                 135                 140 cat cat acc aat gtg att tat att gag aaa aac ggc gaa tta ctg ttt     480
His His Thr Asn Val Ile Tyr Ile Glu Lys Asn Gly Glu Leu Leu Phe
145                 150                 155                 160 tcc aag cct tgc gta gta gaa agt gaa aat gcg gaa aat gtt ttc gca     528
Ser Lys Pro Cys Val Val Glu Ser Glu Asn Ala Glu Asn Val Phe Ala
                165                 170                 175 aac tta aat gcg aaa gat att tat gat ttt tct tta aat gtg gag ctg     576
Asn Leu Asn Ala Lys Asp Ile Tyr Asp Phe Ser Leu Asn Val Glu Leu
                180                 185                 190
```

```
gag aag att cgc ttt att caa cag gcg gca att tta aat agt gcg ctt      624
Glu Lys Ile Arg Phe Ile Gln Gln Ala Ala Ile Leu Asn Ser Ala Leu
            195                 200                 205 tca caa gaa ggg ctg aat caa gat tac ggt tta cat atc ggg cgt acc      672
Ser Gln Glu Gly Leu Asn Gln Asp Tyr Gly Leu His Ile Gly Arg Thr
        210                 215                 220 ttg caa aaa caa att ggt aaa gga tta att agc gat gat ttg ctt aat      720
Leu Gln Lys Gln Ile Gly Lys Gly Leu Ile Ser Asp Asp Leu Leu Asn
225                 230                 235                 240 cgt atc gtg att gaa act acc gct gcc agc gat gca cgc atg ggc ggc      768
Arg Ile Val Ile Glu Thr Thr Ala Ala Ser Asp Ala Arg Met Gly Gly
                245                 250                 255 gca aat tta ccg gcg atg agt aat tcg ggt tcc ggc aac caa ggg att      816
Ala Asn Leu Pro Ala Met Ser Asn Ser Gly Ser Gly Asn Gln Gly Ile
            260                 265                 270 act gcg aca atg ccg gtg gtc gtg gtc gcc cgt cat tta gtt gcg agt      864
Thr Ala Thr Met Pro Val Val Val Val Ala Arg His Leu Val Ala Ser
        275                 280                 285 gaa gaa caa ctg att cga gcg tta ttt ctt tcg cat tta atg gcg att      912
Glu Glu Gln Leu Ile Arg Ala Leu Phe Leu Ser His Leu Met Ala Ile
    290                 295                 300 tat att cat agc aaa tta ccg aaa ctc tct gcg tta tgt gcg gtc act      960
Tyr Ile His Ser Lys Leu Pro Lys Leu Ser Ala Leu Cys Ala Val Thr
305                 310                 315                 320 acg gcg gca atg ggc agc tgt gcc ggc gtc gca tgg tta tta acc ggt     1008
Thr Ala Ala Met Gly Ser Cys Ala Gly Val Ala Trp Leu Leu Thr Gly
                325                 330                 335 aaa ttt gaa gcg atc agt atg gca atc agc agt atg atc ggt gat att     1056
Lys Phe Glu Ala Ile Ser Met Ala Ile Ser Ser Met Ile Gly Asp Ile
            340                 345                 350 agc ggc att att tgt gac ggt gcg gca aat agc tgc gcg atg aaa gtt     1104
Ser Gly Ile Ile Cys Asp Gly Ala Ala Asn Ser Cys Ala Met Lys Val
        355                 360                 365 tca acc agt gtg agt tcc agt tat aaa tcg att tta atg gca ttg gac     1152
Ser Thr Ser Val Ser Ser Ser Tyr Lys Ser Ile Leu Met Ala Leu Asp
    370                 375                 380 gac acc caa gtg act ggt aac gaa ggg att gtc gaa cac caa atc gac     1200
Asp Thr Gln Val Thr Gly Asn Glu Gly Ile Val Glu His Gln Ile Asp
385                 390                 395                 400 cgt tcg atc aac aac ctt tgt gcg ata gct tcc cgc agt atg caa tat     1248
Arg Ser Ile Asn Asn Leu Cys Ala Ile Ala Ser Arg Ser Met Gln Tyr
                405                 410                 415 act gat cgc caa gtg att gag att atg gtg agc aag ccg aaa agc ctg     1296
Thr Asp Arg Gln Val Ile Glu Ile Met Val Ser Lys Pro Lys Ser Leu
            420                 425                 430 taa                                                                 1299

<210> SEQ ID NO 27
<211> LENGTH: 432
<212> TYPE: PRT
<213> ORGANISM: Actinobacillus pleuropneumoniae

<400> SEQUENCE: 27

Met Lys Phe Lys Ser Glu Leu Glu Gln Ala Ile Ile Ala Thr Val Gln
1               5                   10                  15

Gln Glu Val Val Pro Ala Leu Gly Cys Thr Glu Pro Val Ser Leu Ala
            20                  25                  30

Leu Ala Ala Ala Val Ala Arg Gln Tyr Leu Gly Ala Leu Pro Asp Arg
        35                  40                  45

Ile Glu Ala Lys Val Ser Pro Asn Leu Met Lys Asn Gly Met Gly Val
```

|  |  |  | 50 |  |  |  | 55 |  |  |  | 60 |  |
|--|--|--|--|--|--|--|--|--|--|--|--|--|

Thr Val Pro Gly Thr Gly Thr Val Gly Leu Thr Met Ala Ala Ala Ile
65                  70                  75                  80

Gly Ala Ile Gly Gly Asp Pro Asn Gly Gly Leu Glu Val Leu Lys His
                85                  90                  95

Ile Thr Asn Glu Gln Val Ala Gln Ala Lys Gln Met Ile His Asp His
            100                 105                 110

Lys Ile Glu Val Ser Ile Ser Asp Thr Glu His Ile Leu Tyr Ser Glu
            115                 120                 125

Ala Thr Leu Phe Asn Ala Asp Gln Gln Val Lys Val Arg Ile Ala Ala
130                 135                 140

His His Thr Asn Val Ile Tyr Ile Glu Lys Asn Gly Glu Leu Leu Phe
145                 150                 155                 160

Ser Lys Pro Cys Val Val Glu Ser Glu Asn Ala Glu Asn Val Phe Ala
                165                 170                 175

Asn Leu Asn Ala Lys Asp Ile Tyr Asp Phe Ser Leu Asn Val Glu Leu
            180                 185                 190

Glu Lys Ile Arg Phe Ile Gln Gln Ala Ala Ile Leu Asn Ser Ala Leu
            195                 200                 205

Ser Gln Glu Gly Leu Asn Gln Asp Tyr Gly Leu His Ile Gly Arg Thr
210                 215                 220

Leu Gln Lys Gln Ile Gly Lys Gly Leu Ile Ser Asp Asp Leu Leu Asn
225                 230                 235                 240

Arg Ile Val Ile Glu Thr Thr Ala Ala Ser Asp Ala Arg Met Gly Gly
                245                 250                 255

Ala Asn Leu Pro Ala Met Ser Asn Ser Gly Ser Gly Asn Gln Gly Ile
            260                 265                 270

Thr Ala Thr Met Pro Val Val Val Ala Arg His Leu Val Ala Ser
            275                 280                 285

Glu Glu Gln Leu Ile Arg Ala Leu Phe Leu Ser His Leu Met Ala Ile
290                 295                 300

Tyr Ile His Ser Lys Leu Pro Lys Leu Ser Ala Leu Cys Ala Val Thr
305                 310                 315                 320

Thr Ala Ala Met Gly Ser Cys Ala Gly Val Ala Trp Leu Leu Thr Gly
                325                 330                 335

Lys Phe Glu Ala Ile Ser Met Ala Ser Ser Met Ile Gly Asp Ile
            340                 345                 350

Ser Gly Ile Ile Cys Asp Gly Ala Ala Asn Ser Cys Ala Met Lys Val
            355                 360                 365

Ser Thr Ser Val Ser Ser Ser Tyr Lys Ser Ile Leu Met Ala Leu Asp
370                 375                 380

Asp Thr Gln Val Thr Gly Asn Glu Gly Ile Val Glu His Gln Ile Asp
385                 390                 395                 400

Arg Ser Ile Asn Asn Leu Cys Ala Ile Ala Ser Arg Ser Met Gln Tyr
                405                 410                 415

Thr Asp Arg Gln Val Ile Glu Ile Met Val Ser Lys Pro Lys Ser Leu
            420                 425                 430

<210> SEQ ID NO 28
<211> LENGTH: 1278
<212> TYPE: DNA
<213> ORGANISM: Klebsiella pneumoniae
<220> FEATURE:
<221> NAME/KEY: CDS
<222> LOCATION: (1)..(1278)

<400> SEQUENCE: 28

```
atg aac acc gat aac gct tcc ctg tac gta aaa tgg ctc aaa caa gag      48
Met Asn Thr Asp Asn Ala Ser Leu Tyr Val Lys Trp Leu Lys Gln Glu
1               5                   10                  15 gtc gcc ccg gct tta ggt tgt act gaa ccc gtc gct att tcc ttc gcg      96
Val Ala Pro Ala Leu Gly Cys Thr Glu Pro Val Ala Ile Ser Phe Ala
            20                  25                  30 gcc gcc tac gcc gca caa tat ctg gat cag cct tgc act aaa att agc     144
Ala Ala Tyr Ala Ala Gln Tyr Leu Asp Gln Pro Cys Thr Lys Ile Ser
        35                  40                  45 ggt ttt att tcc gcc aat ctt tat aaa aac gcg atg ggc gtc acc ata     192
Gly Phe Ile Ser Ala Asn Leu Tyr Lys Asn Ala Met Gly Val Thr Ile
    50                  55                  60 ccc ggc acc acc gtt tgc ggt gta ccg ctg gca gcc gca att ggc gca     240
Pro Gly Thr Thr Val Cys Gly Val Pro Leu Ala Ala Ala Ile Gly Ala
65                  70                  75                  80 ttt ggc ggc gac ccg caa aag gga tta aaa acg ctg gaa gat atc act     288
Phe Gly Gly Asp Pro Gln Lys Gly Leu Lys Thr Leu Glu Asp Ile Thr
                85                  90                  95 ccg caa cac gtt gaa atg gcg cag aag ctg atc gcc aat aac gcc gtt     336
Pro Gln His Val Glu Met Ala Gln Lys Leu Ile Ala Asn Asn Ala Val
            100                 105                 110 gat att gcc gtc gaa gag act cct gat ttt att cat ctc gat cta acc     384
Asp Ile Ala Val Glu Glu Thr Pro Asp Phe Ile His Leu Asp Leu Thr
        115                 120                 125 ctc tct gct ggc gat aat tgc tgt cgt gtc gtg gtc aaa gga acc cac     432
Leu Ser Ala Gly Asp Asn Cys Cys Arg Val Val Val Lys Gly Thr His
    130                 135                 140 acc aac gtg gtc gaa ctt tat att aat ggc cag ccg cag cca tta agc     480
Thr Asn Val Val Glu Leu Tyr Ile Asn Gly Gln Pro Gln Pro Leu Ser
145                 150                 155                 160 gaa aaa cag aat acg cgc acc cag cgc gaa acg ctg ccc act ttc tcg     528
Glu Lys Gln Asn Thr Arg Thr Gln Arg Glu Thr Leu Pro Thr Phe Ser
                165                 170                 175 cta caa cag gct tac gac ttt att aat cgc gtc gac ttt aat gat att     576
Leu Gln Gln Ala Tyr Asp Phe Ile Asn Arg Val Asp Phe Asn Asp Ile
            180                 185                 190 cgc ttt att ctc gac gcc gcg cgc tta aac tcc gcg ctg gcg gca gaa     624
Arg Phe Ile Leu Asp Ala Ala Arg Leu Asn Ser Ala Leu Ala Ala Glu
        195                 200                 205 ggc aaa aca aaa aaa tat ggc ctg aac att aac ggt acc ttt tct gac     672
Gly Lys Thr Lys Lys Tyr Gly Leu Asn Ile Asn Gly Thr Phe Ser Asp
    210                 215                 220 gca gtg aaa aac ggc ctg atg agc aac gat ctg tta agc aag gtg atc     720
Ala Val Lys Asn Gly Leu Met Ser Asn Asp Leu Leu Ser Lys Val Ile
225                 230                 235                 240 atc aac acc gtc gcc gct tca gat gcc cgc atg ggc ggc gcg ccg gtg     768
Ile Asn Thr Val Ala Ala Ser Asp Ala Arg Met Gly Gly Ala Pro Val
                245                 250                 255 gta gcg atg tct aac ttc ggc tca ggc aat cag ggc att aca gca acc     816
Val Ala Met Ser Asn Phe Gly Ser Gly Asn Gln Gly Ile Thr Ala Thr
            260                 265                 270 atg ccg gta gtg gtg gtt gca gag cat ctc ggc gtc gat gaa gag acc     864
Met Pro Val Val Val Val Ala Glu His Leu Gly Val Asp Glu Glu Thr
        275                 280                 285 ctg gct cgc gct ttg tct ctc tct cat ctc acc gcc atc tca att cat     912
Leu Ala Arg Ala Leu Ser Leu Ser His Leu Thr Ala Ile Ser Ile His
    290                 295                 300 tct cgt tac acg cgc tta tct gcg cta tgc gca gcc tca acc gcc gct     960
Ser Arg Tyr Thr Arg Leu Ser Ala Leu Cys Ala Ala Ser Thr Ala Ala
```

```
                    305                 310                 315                 320
atg ggc gcc gcc gcc ggt atg gcc tgg ctg ttt acc cgc gac atc aac              1008
Met Gly Ala Ala Ala Gly Met Ala Trp Leu Phe Thr Arg Asp Ile Asn
                    325                 330                 335 acg att aat acc gcg att att aat atg atc agc gat att acc ggc atg              1056
Thr Ile Asn Thr Ala Ile Ile Asn Met Ile Ser Asp Ile Thr Gly Met
            340                 345                 350 att tgt gat ggc gct tcc aac agc tgc gcg atg aaa gtc tcg tca gtg              1104
Ile Cys Asp Gly Ala Ser Asn Ser Cys Ala Met Lys Val Ser Ser Val
        355                 360                 365 gta tcc agc gcc ttt aag gcg gta cta atg gcc atg caa aat agc tgt              1152
Val Ser Ser Ala Phe Lys Ala Val Leu Met Ala Met Gln Asn Ser Cys
    370                 375                 380 gct ggc gcc aat gac ggt att gtc tgc gct gat gtt gag caa acc att              1200
Ala Gly Ala Asn Asp Gly Ile Val Cys Ala Asp Val Glu Gln Thr Ile
385                 390                 395                 400 aat aac tta tgc cgt ctg gtg att aaa cca atg act ctc acc gat aaa              1248
Asn Asn Leu Cys Arg Leu Val Ile Lys Pro Met Thr Leu Thr Asp Lys
                405                 410                 415 gaa att atc agc att atg gtc gct aaa taa                                       1278
Glu Ile Ile Ser Ile Met Val Ala Lys
                420                 425

<210> SEQ ID NO 29
<211> LENGTH: 425
<212> TYPE: PRT
<213> ORGANISM: Klebsiella pneumoniae

<400> SEQUENCE: 29

Met Asn Thr Asp Asn Ala Ser Leu Tyr Val Lys Trp Leu Lys Gln Glu
1               5                   10                  15

Val Ala Pro Ala Leu Gly Cys Thr Glu Pro Val Ala Ile Ser Phe Ala
            20                  25                  30

Ala Ala Tyr Ala Ala Gln Tyr Leu Asp Gln Pro Cys Thr Lys Ile Ser
        35                  40                  45

Gly Phe Ile Ser Ala Asn Leu Tyr Lys Asn Ala Met Gly Val Thr Ile
    50                  55                  60

Pro Gly Thr Thr Val Cys Gly Val Pro Leu Ala Ala Ile Gly Ala
65                  70                  75                  80

Phe Gly Gly Asp Pro Gln Lys Gly Leu Lys Thr Leu Glu Asp Ile Thr
                85                  90                  95

Pro Gln His Val Glu Met Ala Gln Lys Leu Ile Ala Asn Asn Ala Val
            100                 105                 110

Asp Ile Ala Val Glu Glu Thr Pro Asp Phe Ile His Leu Asp Leu Thr
        115                 120                 125

Leu Ser Ala Gly Asp Asn Cys Cys Arg Val Val Lys Gly Thr His
    130                 135                 140

Thr Asn Val Val Glu Leu Tyr Ile Asn Gly Pro Gln Pro Leu Ser
145                 150                 155                 160

Glu Lys Gln Asn Thr Arg Thr Gln Arg Glu Thr Leu Pro Thr Phe Ser
                165                 170                 175

Leu Gln Gln Ala Tyr Asp Phe Ile Asn Arg Val Asp Phe Asn Asp Ile
            180                 185                 190

Arg Phe Ile Leu Asp Ala Ala Arg Leu Asn Ser Ala Leu Ala Ala Glu
        195                 200                 205

Gly Lys Thr Lys Lys Tyr Gly Leu Asn Ile Asn Gly Thr Phe Ser Asp
    210                 215                 220
```

```
Ala Val Lys Asn Gly Leu Met Ser Asn Asp Leu Leu Ser Lys Val Ile
225                 230                 235                 240

Ile Asn Thr Val Ala Ala Ser Asp Ala Arg Met Gly Gly Ala Pro Val
                245                 250                 255

Val Ala Met Ser Asn Phe Gly Ser Gly Asn Gln Gly Ile Thr Ala Thr
            260                 265                 270

Met Pro Val Val Val Ala Glu His Leu Gly Val Asp Glu Glu Thr
        275                 280                 285

Leu Ala Arg Ala Leu Ser Leu Ser His Leu Thr Ala Ile Ser Ile His
    290                 295                 300

Ser Arg Tyr Thr Arg Leu Ser Ala Leu Cys Ala Ala Ser Thr Ala Ala
305                 310                 315                 320

Met Gly Ala Ala Gly Met Ala Trp Leu Phe Thr Arg Asp Ile Asn
                325                 330                 335

Thr Ile Asn Thr Ala Ile Ile Asn Met Ile Ser Asp Ile Thr Gly Met
                340                 345                 350

Ile Cys Asp Gly Ala Ser Asn Ser Cys Ala Met Lys Val Ser Ser Val
                355                 360                 365

Val Ser Ser Ala Phe Lys Ala Val Leu Met Ala Met Gln Asn Ser Cys
    370                 375                 380

Ala Gly Ala Asn Asp Gly Ile Val Cys Ala Asp Val Glu Gln Thr Ile
385                 390                 395                 400

Asn Asn Leu Cys Arg Leu Val Ile Lys Pro Met Thr Leu Thr Asp Lys
                405                 410                 415

Glu Ile Ile Ser Ile Met Val Ala Lys
            420                 425

<210> SEQ ID NO 30
<211> LENGTH: 1278
<212> TYPE: DNA
<213> ORGANISM: Vibrio fischeri
<220> FEATURE:
<221> NAME/KEY: CDS
<222> LOCATION: (1)..(1278)

<400> SEQUENCE: 30 atg aac tct atc tgg aaa cag tac att gat att tta caa ggt gtt gta        48
Met Asn Ser Ile Trp Lys Gln Tyr Ile Asp Ile Leu Gln Gly Val Val
1               5                   10                  15 aaa cca gct ctt ggt tgt act gaa cca att tgt gcc gct tat gct gca        96
Lys Pro Ala Leu Gly Cys Thr Glu Pro Ile Cys Ala Ala Tyr Ala Ala
                20                  25                  30 agc gtg gct aca caa atg ctt ggt tct aaa cca gaa aca ata gac gtt       144
Ser Val Ala Thr Gln Met Leu Gly Ser Lys Pro Glu Thr Ile Asp Val
            35                  40                  45 ttt gtt tct gat aac tta tac aaa aat agc atg ggt gtt ttt gta cca       192
Phe Val Ser Asp Asn Leu Tyr Lys Asn Ser Met Gly Val Phe Val Pro
        50                  55                  60 aga aca ggt aga gtt ggc ctt gct att gca gcg gca act ggg gca ata       240
Arg Thr Gly Arg Val Gly Leu Ala Ile Ala Ala Ala Thr Gly Ala Ile
65                  70                  75                  80 ggt ggt aat cct gat gca ggc tta gaa gta tta gca aag ata act gaa       288
Gly Gly Asn Pro Asp Ala Gly Leu Glu Val Leu Ala Lys Ile Thr Glu
                85                  90                  95 gaa gaa gta gat gaa gca caa aag ctc att gat aat ggc tgt gta gtc       336
Glu Glu Val Asp Glu Ala Gln Lys Leu Ile Asp Asn Gly Cys Val Val
            100                 105                 110 gtt caa aga gaa acc act gac gag ttt att tat tgt cga gtt att gct       384
Val Gln Arg Glu Thr Thr Asp Glu Phe Ile Tyr Cys Arg Val Ile Ala
```

|  |  |  |  |  |  |  |  |  |  |  |  |  |
|---|---|---|---|---|---|---|---|---|---|---|---|---|
|  |  | 115 |  |  |  | 120 |  |  |  | 125 |  |  |

```
aaa aat gcg gtt cat aat gct gaa gtt acg att agc ggt ggt cac act     432
Lys Asn Ala Val His Asn Ala Glu Val Thr Ile Ser Gly Gly His Thr
    130                 135                 140 cta att att gaa aaa cgt ctt gat gat aac gtc att ttc acg ctg gat     480
Leu Ile Ile Glu Lys Arg Leu Asp Asp Asn Val Ile Phe Thr Leu Asp
145                 150                 155                 160 tcc tct tta cca aaa aca tct aca gcg tca att tgt gat ggc gtt gat     528
Ser Ser Leu Pro Lys Thr Ser Thr Ala Ser Ile Cys Asp Gly Val Asp
                165                 170                 175 atc act atc tca tca att tat gac ttt gct acc caa gca gag ttt gac     576
Ile Thr Ile Ser Ser Ile Tyr Asp Phe Ala Thr Gln Ala Glu Phe Asp
            180                 185                 190 gac att aaa ttt att tta gag gca aaa gag tta aat atc gct ctc gct     624
Asp Ile Lys Phe Ile Leu Glu Ala Lys Glu Leu Asn Ile Ala Leu Ala
        195                 200                 205 caa gaa ggt tta aat aac cct tac ggt tta gaa gtc ggc cga acc tat     672
Gln Glu Gly Leu Asn Asn Pro Tyr Gly Leu Glu Val Gly Arg Thr Tyr
    210                 215                 220 caa aag aac att gaa aaa gga tta ctt gct aaa agt cta gat agt gac     720
Gln Lys Asn Ile Glu Lys Gly Leu Leu Ala Lys Ser Leu Asp Ser Asp
225                 230                 235                 240 att ttg atc tat act tct gca gca tct gac gct cgt atg gga ggg gcg     768
Ile Leu Ile Tyr Thr Ser Ala Ala Ser Asp Ala Arg Met Gly Gly Ala
                245                 250                 255 aca cta cca gcc atg tcg aat tat ggc agt ggt aac caa ggt att gca     816
Thr Leu Pro Ala Met Ser Asn Tyr Gly Ser Gly Asn Gln Gly Ile Ala
            260                 265                 270 gca act att cca gta gta aaa atg gct gac ttt ttt aat gct gat gat     864
Ala Thr Ile Pro Val Val Lys Met Ala Asp Phe Phe Asn Ala Asp Asp
        275                 280                 285 gaa aaa tta gct cga gct ttt atc atg agt cat ctt ggt gcc att tat     912
Glu Lys Leu Ala Arg Ala Phe Ile Met Ser His Leu Gly Ala Ile Tyr
    290                 295                 300 att aaa tct cac tac cca cca ctt tct gct ttt tgt ggt aat gct gtt     960
Ile Lys Ser His Tyr Pro Pro Leu Ser Ala Phe Cys Gly Asn Ala Val
305                 310                 315                 320 act tct gca gca gca tca atg gcg atg gta tat cta gct ggt ggc acg    1008
Thr Ser Ala Ala Ala Ser Met Ala Met Val Tyr Leu Ala Gly Gly Thr
                325                 330                 335 ttt gaa caa tct tgc tca gcc att caa aat acc atc agt gat acc agc    1056
Phe Glu Gln Ser Cys Ser Ala Ile Gln Asn Thr Ile Ser Asp Thr Ser
            340                 345                 350 ggt atg att tgt gac ggt gca aaa tca acg tgt gcg atg aaa gtg gga    1104
Gly Met Ile Cys Asp Gly Ala Lys Ser Thr Cys Ala Met Lys Val Gly
        355                 360                 365 agt agc gct caa tca gca atg aaa tct gct cta tta gca cta aat gat    1152
Ser Ser Ala Gln Ser Ala Met Lys Ser Ala Leu Leu Ala Leu Asn Asp
    370                 375                 380 cat tgt gta acg aag caa ggt gtg att gct gat gat gtt gaa aag aca    1200
His Cys Val Thr Lys Gln Gly Val Ile Ala Asp Asp Val Glu Lys Thr
385                 390                 395                 400 att aaa aac att ggc aga atg atc aca aca ggt atg cct aat att gat    1248
Ile Lys Asn Ile Gly Arg Met Ile Thr Thr Gly Met Pro Asn Ile Asp
                405                 410                 415 cat gaa atc att gaa ata atg gcg tca taa                            1278
His Glu Ile Ile Glu Ile Met Ala Ser
            420                 425
```

<210> SEQ ID NO 31

```
<211> LENGTH: 425
<212> TYPE: PRT
<213> ORGANISM: Vibrio fischeri

<400> SEQUENCE: 31

Met Asn Ser Ile Trp Lys Gln Tyr Ile Asp Ile Leu Gln Gly Val Val
1               5                   10                  15

Lys Pro Ala Leu Gly Cys Thr Glu Pro Ile Cys Ala Ala Tyr Ala Ala
            20                  25                  30

Ser Val Ala Thr Gln Met Leu Gly Ser Lys Pro Glu Thr Ile Asp Val
        35                  40                  45

Phe Val Ser Asp Asn Leu Tyr Lys Asn Ser Met Gly Val Phe Val Pro
    50                  55                  60

Arg Thr Gly Arg Val Gly Leu Ala Ile Ala Ala Thr Gly Ala Ile
65                  70                  75                  80

Gly Gly Asn Pro Asp Ala Gly Leu Glu Val Leu Ala Lys Ile Thr Glu
                85                  90                  95

Glu Glu Val Asp Glu Ala Gln Lys Leu Ile Asp Asn Gly Cys Val Val
            100                 105                 110

Val Gln Arg Glu Thr Thr Asp Glu Phe Ile Tyr Cys Arg Val Ile Ala
        115                 120                 125

Lys Asn Ala Val His Asn Ala Glu Val Thr Ile Ser Gly Gly His Thr
130                 135                 140

Leu Ile Ile Glu Lys Arg Leu Asp Asp Asn Val Ile Phe Thr Leu Asp
145                 150                 155                 160

Ser Ser Leu Pro Lys Thr Ser Thr Ala Ser Ile Cys Asp Gly Val Asp
                165                 170                 175

Ile Thr Ile Ser Ser Ile Tyr Asp Phe Ala Thr Gln Ala Glu Phe Asp
            180                 185                 190

Asp Ile Lys Phe Ile Leu Glu Ala Lys Glu Leu Asn Ile Ala Leu Ala
        195                 200                 205

Gln Glu Gly Leu Asn Asn Pro Tyr Gly Leu Glu Val Gly Arg Thr Tyr
    210                 215                 220

Gln Lys Asn Ile Glu Lys Gly Leu Leu Ala Lys Ser Leu Asp Ser Asp
225                 230                 235                 240

Ile Leu Ile Tyr Thr Ser Ala Ala Ser Asp Ala Arg Met Gly Gly Ala
                245                 250                 255

Thr Leu Pro Ala Met Ser Asn Tyr Gly Ser Gly Asn Gln Gly Ile Ala
            260                 265                 270

Ala Thr Ile Pro Val Val Lys Met Ala Asp Phe Phe Asn Ala Asp Asp
        275                 280                 285

Glu Lys Leu Ala Arg Ala Phe Ile Met Ser His Leu Gly Ala Ile Tyr
    290                 295                 300

Ile Lys Ser His Tyr Pro Pro Leu Ser Ala Phe Cys Gly Asn Ala Val
305                 310                 315                 320

Thr Ser Ala Ala Ala Ser Met Ala Met Val Tyr Leu Ala Gly Thr
                325                 330                 335

Phe Glu Gln Ser Cys Ser Ala Ile Gln Asn Thr Ile Ser Asp Thr Ser
            340                 345                 350

Gly Met Ile Cys Asp Gly Ala Lys Ser Thr Cys Ala Met Lys Val Gly
        355                 360                 365

Ser Ser Ala Gln Ser Ala Met Lys Ser Ala Leu Leu Ala Leu Asn Asp
    370                 375                 380

His Cys Val Thr Lys Gln Gly Val Ile Ala Asp Asp Val Glu Lys Thr
385                 390                 395                 400
```

```
Ile Lys Asn Ile Gly Arg Met Ile Thr Thr Gly Met Pro Asn Ile Asp
            405                 410                 415

His Glu Ile Ile Glu Ile Met Ala Ser
            420             425
```

L-CYSTEINE-PRODUCING BACTERIUM AND A METHOD FOR PRODUCING L-CYSTEINE

This application claims priority under 35 U.S.C. §119 to Japanese Patent Application No. 2008-056362, filed on Mar. 6, 2008, which is incorporated in its entirety by reference. The Sequence Listing in electronic format filed herewith is also hereby incorporated by reference in its entirety (File Name: US-385_Seq_List; File Size: 72 KB; Date Created: Mar. 4, 2009).

BACKGROUND OF THE INVENTION

1. Field of the Invention

The present invention relates to a method for producing L-cysteine or related substances. Specifically, the present invention relates to a bacterium suitable for the production of L-cysteine or related substances and a method for producing L-cysteine or related substances utilizing such a bacterium. L-cysteine and L-cysteine-related substances are used in the fields of drugs, cosmetics, and foods.

2. Brief Description of the Related Art

L-cysteine is conventionally obtained by extraction from keratin-containing substances such as hairs, horns, and feathers, or by conversion of DL-2-aminothiazoline-4-carboxylic acid using a microbial enzyme. L-cysteine has also been produced on a large scale by using an immobilized enzyme method and a novel enzyme. Furthermore, it has also been attempted to produce L-cysteine by fermentation utilizing a microorganism.

Microorganisms which are able to produce L-cysteine are known. For example, a coryneform bacterium with increased intracellular serine acetyltransferase activity produces cysteine (Japanese Patent Laid-open (Kokai) No. 2002-233384). L-cysteine-producing ability can also be increased by incorporating serine acetyltransferase which has been mutated to attenuate feedback inhibition by L-cysteine (Japanese Patent Laid-open No. 11-155571, U.S. Patent Published Application No. 20050112731, U.S. Pat. No. 6,218,168).

Furthermore, L-cysteine-producing ability in a microorganism can be enhanced by suppressing the L-cysteine decomposition system. Examples of such microorganisms include coryneform bacteria or *Escherichia* bacteria in which the activity of cystathionine-β-lyase (U.S. Patent Published Application No. 20050112731), tryptophanase (Japanese Patent Laid-open No. 2003-169668), or O-acetylserine sulfhydrylase B (Japanese Patent Laid-open No. 2005-245311) is attenuated or deleted.

Furthermore, it is known that the ydeD gene which encodes the YdeD protein participates in secretion of the metabolic products of the cysteine pathway (Dabler et al., Mol. Microbiol., 36, 1101-1112 (2000)). Furthermore, techniques of enhancing L-cysteine-producing ability by increasing expression of the mar-locus, emr-locus, acr-locus, cmr-locus, mex-gene, bmr-gene, or qacA-gene, are also known. These loci and/or genes encode proteins which cause secretion of toxic substances from cells (U.S. Pat. No. 5,972,663). emrAB, emrKY, yojIH, acrEF, bcr, and cusA are further examples (Japanese Patent Laid-open No. 2005-287333).

An *Escherichia coli* has been reported which produces L-cysteine, and which has increased activity of the positive transcriptional control factor of the cysteine regulon encoded by the cysB gene (International Patent Publication WO01/27307).

yhaM is registered at the database EcoCyc (BioCyc Home Page, Summary of *Escherichia coli*, Strain K-12, version 11.6, *E. coli* K-12 Gene: yhaM, biocyc.org/ECOLI/NEW-IMAGE?type=GENE&object=G7622) as a gene of unknown function, and it's relation with L-cysteine production is also unknown.

SUMMARY OF THE INVENTION

The present invention provides a novel technique for improving bacterial L-cysteine-producing ability, and thereby provides an L-cysteine-producing bacterium, as well as a method for producing L-cysteine, L-cystine, their derivatives, or a mixture of these by using such a bacterium.

L-cysteine-producing ability of a bacterium is enhanced by modifying the bacterium so that the activity of the protein encoded by the yhaM gene is decreased.

It is an aspect of the present invention to provide a bacterium belonging to the family Enterobacteriaceae, which has L-cysteine-producing ability and has been modified to decrease the activity of the protein encoded by the yhaM gene as compared to the unmodified bacterium.

It is a further aspect of the present invention to provide the aforementioned bacterium, wherein the activity of the protein is decreased by attenuating expression of the yhaM gene or by disrupting the gene.

It is a further aspect of the present invention to provide the aforementioned bacterium, wherein the protein is selected from the group consisting of:

(A) a protein comprising the amino acid sequence of SEQ ID NO: 2, and (B) a protein comprising the amino acid sequence of SEQ ID NO: 2, but which includes substitutions, deletions, insertions or additions of one or several amino acid residues, and wherein L-cysteine-producing ability of the bacterium is improved as compared to an unmodified bacterium.

It is a further aspect of the present invention to provide the aforementioned bacterium, wherein the yhaM gene is selected from the group consisting of:

(a) a DNA comprising the nucleotide sequence of SEQ ID NO: 1, and (b) a DNA which is able to hybridize with a sequence complementary to the nucleotide sequence of SEQ ID NO: 1 or a probe which is prepared from the nucleotide sequence, under stringent conditions, and wherein L-cysteine-producing ability of the bacterium is improved as compared to an unmodified bacterium.

It is a further aspect of the present invention to provide the aforementioned bacterium, in which serine acetyltransferase has been mutated so that feedback inhibition by L-cysteine is attenuated.

It is a further aspect of the present invention to provide the aforementioned bacterium, which is an *Escherichia* bacterium.

It is a further aspect of the present invention to provide the aforementioned bacterium, which is *Escherichia coli*.

It is a further aspect of the present invention to provide a method for producing an L-amino acid selected from the group consisting of L-cysteine, L-cystine, a derivative thereof, and combinations thereof, which comprises culturing the aforementioned bacterium in a medium and collecting the L-amino acid from the medium.

It is a further aspect of the present invention to provide the aforementioned method, wherein the derivative of L-cysteine is a thiazolidine derivative.

According to the present invention, L-cysteine-producing ability of bacteria can be improved. Furthermore, according to the present invention, L-cysteine, L-cystine, their derivatives, or combinations thereof can be efficiently produced.

DETAILED DESCRIPTION OF EXEMPLARY EMBODIMENTS

<1> Bacterium

Figure 1:
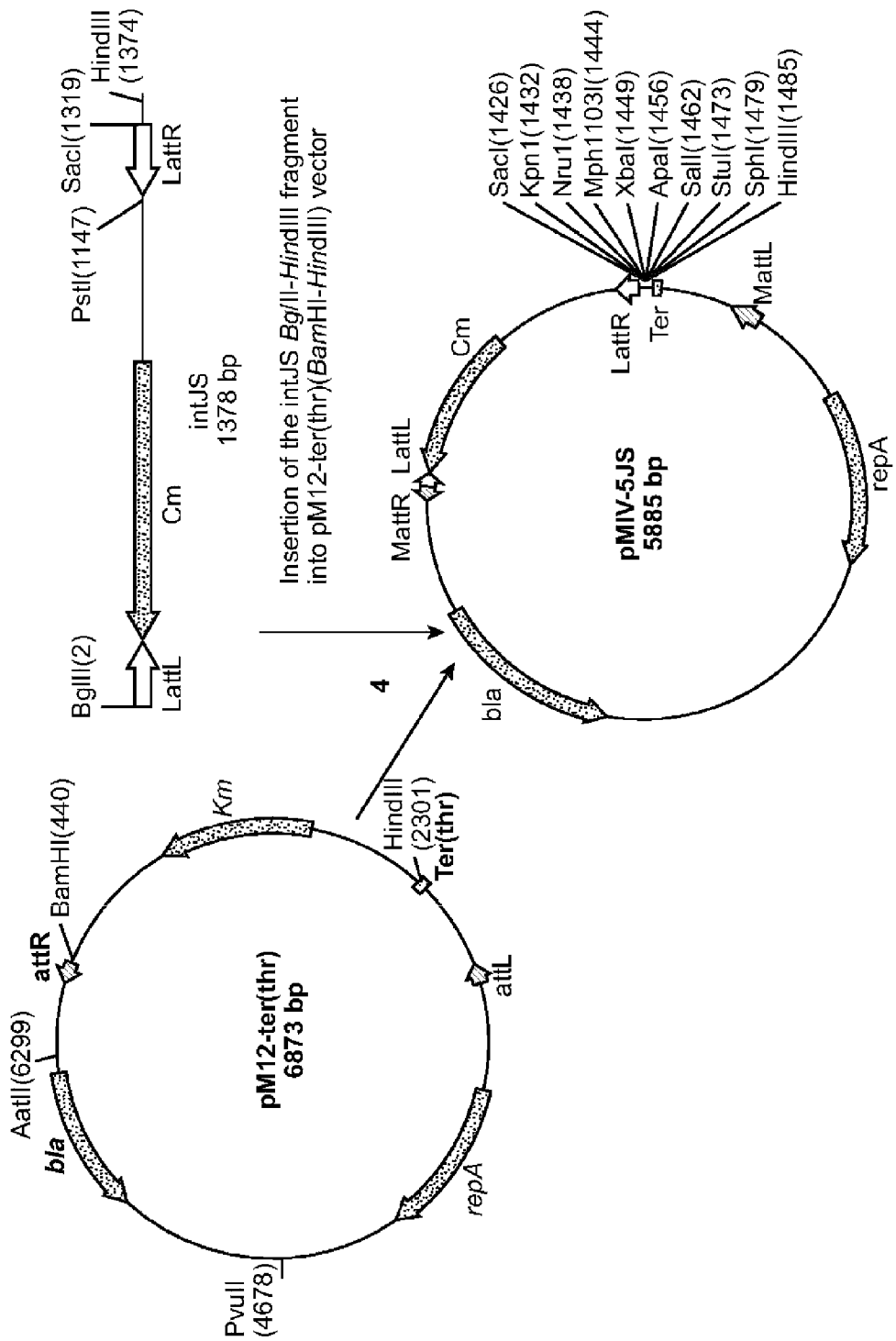
FIG. 1 shows the construction of the pMIV-5JS plasmid.

The bacterium belongs to the family Enterobacteriaceae, and is able to produce L-cysteine. Furthermore, the bacterium has been modified to decrease the activity of the protein encoded by the yhaM gene. The "ability to produce L-cysteine" or the "L-cysteine-producing ability" means an ability of the bacterium to produce L-cysteine and cause accumulation of L-cysteine in a medium or the bacterial cells in such an amount that the L-cysteine can be collected from the medium or cells when the bacterium is cultured in the medium. A bacterium having L-cysteine-producing ability means a bacterium which can produce and cause accumulation of a larger amount of L-cysteine as compared with a wild-type, parent, or unmodified strain, and preferably a bacterium which can produce and cause accumulation of L-cysteine in a medium in an amount of 0.05 g/L or more, more preferably 0.1 g/L or more, particularly preferably 0.2 g/L or more.

The L-cysteine produced by the bacterium may change into L-cystine in the medium by the formation of a disulfide bond. Furthermore, as described later, S-sulfocysteine may be generated by the reaction of L-cysteine and thiosulfuric acid in the medium (Szczepkowski T. W., Nature, vol. 182 (1958)). Furthermore, the L-cysteine generated in bacterial cells may be condensed with a ketone, aldehyde, or, for example, pyruvic acid, which is present in the cells, to produce a thiazolidine derivative via an hemithioketal intermediate (refer to Japanese Patent No. 2992010). This thiazolidine derivative and hemithioketal may be present as an equilibrated mixture. Therefore, the L-cysteine-producing ability is not limited to the ability to accumulate only L-cysteine in the medium or cells, but also includes the ability to accumulate L-cystine or its derivative such as S-sulfocysteine, a thiazolidine derivative, or a hemithioketal, or a mixture thereof in the medium.

The bacterium having L-cysteine-producing ability may inherently have the ability to produce L-cysteine, or it may be imparted by modifying a microorganism such as those described below by mutagenesis or a recombinant DNA technique. Unless specially mentioned, the term L-cysteine refers to the reduced-type L-cysteine, L-cystine, derivatives such as those mentioned above, or a mixture thereof.

The bacterium is not particularly limited so long as the bacterium belongs to the family Enterobacteriaceae and has L-cysteine-producing ability. Such bacteria include those of the genera *Escherichia, Enterobacter, Pantoea, Klebsiella, Serratia, Erwinia, Salmonella*, and *Morganella*. Specifically, those classified into the family Enterobacteriaceae according to the taxonomy used in the NCBI (National Center for Biotechnology Information) database www.ncbi.nlm.nih.gov/Taxonomy/Browser/wwwtax.cgi?id=91347) can be used. As the parent strain of the family Enterobacteriaceae which can be used to perform the modification, it is desirable to use, especially, a bacterium of the genus *Escherichia, Enterobacter, Pantoea, Erwinia*, or *Klebsiella*.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. *Escherichia coli* is preferable. Examples of *Escherichia coli* include *Escherichia coli* W3110 (ATCC 27325), *Escherichia coli* MG1655 (ATCC 47076), and so forth, and include those derived from the prototype wild-type strain, K12 strain.

These strains are available from, for example, the American Type Culture Collection (Address: 12301 Parklawn Drive, Rockville, Md. 20852, P.O. Box 1549, Manassas, Va. 20108, United States of America). That is, registration numbers are given to each of the strains, and the strains can be ordered by using these registration numbers (refer to www.atcc.org/). The registration numbers of the strains are listed in the catalogue of the American Type Culture Collection.

Examples of the *Enterobacter* bacteria include *Enterobacter agglomerans, Enterobacter aerogenes* and so forth, and examples of the *Pantoea* bacteria include *Pantoea ananatis*. Some strains of *Enterobacter agglomerans* were recently reclassified into *Pantoea agglomerans, Pantoea ananatis*, or *Pantoea stewartii* on the basis of the nucleotide sequence analysis of 16S rRNA etc. A bacterium belonging to either *Enterobacter* or *Pantoea* may be used so long as it is classified as the family Enterobacteriaceae.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea stewartii* (refer to Int. J. Syst. Bacteriol., 1993, 43:162-173).

Examples of the *Enterobacter* bacteria include, but are not limited to, *Enterobacter agglomerans, Enterobacter aerogenes*, and so forth. Specifically, the strains exemplified in European Patent Publication No. 952221 can be used.

A typical strain of the genus *Enterobacter* is the *Enterobacter agglomeranses* ATCC 12287 strain.

Typical strains of the *Pantoea* bacteria include, but are not limited to, *Pantoea ananatis, Pantoea stewartii, Pantoea agglomerans*, and *Pantoea citrea*.

Specific examples of *Pantoea ananatis* include the *Pantoea ananatis* AJ13355 strain and SC17 strain. The SC17 strain was selected as a low phlegm-producing mutant strain from the AJ13355 strain (FERM BP-6614), which was isolated from soil in Iwata-shi, Shizuoka-ken, Japan for it's ability to proliferate in a low pH medium containing L-glutamic acid and a carbon source (U.S. Pat. No. 6,596,517).

The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was identified as *Enterobacter agglomerans* when it was isolated and deposited as the *Enterobacter agglomerans* AJ13355 strain. However, it was recently reclassified as *Pantoea ananatis* on the basis of nucleotide sequencing of 16S rRNA and so forth.

Examples of the *Erwinia* bacteria include, but are not limited to, *Erwinia amylovora* and *Erwinia carotovora*, and examples of the *Klebsiella* bacteria include *Klebsiella planticola*.

Hereinafter, methods for imparting L-cysteine-producing ability to bacteria belonging to Enterobacteriaceae, or methods for enhancing L-cysteine-producing ability of such bacteria, are described.

To impart the ability to produce L-cysteine, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an analogue-resistant strain, or a metabolic regulation mutant, or by constructing a recombinant strain so that it overexpresses an L-cysteine biosynthesis enzyme. Here, in the breeding of an L-cysteine-producing bacteria, one or more of the above described properties may be imparted. The expression of L-cysteine biosynthesis enzyme(s) can be enhanced alone or in combinations of two or more. Furthermore, imparting properties such as an auxotrophic mutation, analogue resistance, or metabolic regulation mutation may be combined with the methods of enhancing the biosynthesis enzymes.

An auxotrophic mutant strain, L-cysteine analogue-resistant strain, or metabolic regulation mutant strain with the ability to produce L-cysteine can be obtained by subjecting a parent, wild-type, or unmodified strain to conventional mutatagenesis, such as exposure to X-rays or UV irradiation, or by treating with a mutagen such as N-methyl-N'-nitro-N-nitrosoguanidine, etc., then selecting those which exhibit autotrophy, analogue resistance, or a metabolic regulation mutation and which also have the ability to produce L-cysteine.

Specific examples of L-cysteine-producing bacteria include, but are not limited to, *E. coli* JM15 transformed with multiple kinds of cysE gene alleles encoding serine acetyltransferase resistant to feedback inhibition (U.S. Pat. No. 6,218,168), *E. coli* W3110 in which a gene encoding a protein responsible for excretion of cytotoxic substances is overexpressed (U.S. Pat. No. 5,972,663) an *E. coli* strain having decreased cysteine desulfhydrase activity (Japanese Patent Laid-open No. 11-155571), and *E. coli* W3110 with increased activity of the positive transcriptional control factor of the cysteine regulon encoded by the cysB gene (WO01/27307).

The following proteins are known to have the cysteine desulfhydrase activity of *E. coli*: cystathionine-β-lyase (metC product, Japanese Patent Laid-open No. 11-155571, Chandra et al., Biochemistry, 21 (1982) 3064-3069), tryptophanase (tnaA product, Japanese Patent Laid-open No. 2003-169668, Austin Newton et al., J. Biol. Chem., 240 (1965) 1211-1218)), O-acetylserine sulfhydrylase B (cysM gene product, Japanese Patent Laid-open No. 2005-245311), and the malY gene product (Japanese Patent Laid-open No. 2005-245311). By decreasing the activities of these proteins, L-cysteine-producing ability is improved.

The L-cysteine-producing bacterium preferably has a SAT which has been mutated to be resistant to feedback inhibition. The following mutations in SAT are known to induce resistance to feedback inhibition and are derived from *Escherichia coli*: when the methionine residue at position 256 is replaced with a glutamate residue (Japanese Patent Laid-open No. 11-155571), when the methionine residue at position 256 is replaced with an isoleucine residue (Denk, D. and Boeck, A., J. General Microbiol., 133, 515-525 (1987)), a mutation in the region from the amino acid residue at position 97 to the amino acid residue at position 273 or a deletion of the C-terminus region from the amino acid residue at position 227 (International Patent Publication WO97/15673, U.S. Pat. No. 6,218, 168), when the amino acid sequence corresponding to positions 89 to 96 of the wild-type SAT contains one or more mutations (U.S. Patent Published Application No. 20050112731(A1)), and so forth. In the cysE5 gene which encodes the mutant SAT described in the examples, the Val residue and the Asp residue at positions 95 and 96 of the wild-type SAT are replaced with an Arg residue and Pro residue, respectively.

The SAT gene is not limited to the gene of *Escherichia coli*, but can be any gene encoring a protein having the SAT activity. An SAT isozyme of *Arabidopsis thaliana* and desensitized to feedback inhibition by L-cysteine is known, and the gene encoding this SAT can also be used (FEMS Microbiol. Lett., 179 (1999) 453-459).

If a gene encoding a mutant SAT is introduced into a bacterium, L-cysteine-producing ability is imparted to the bacterium. To introduce a mutant SAT gene into a bacterium, various vectors which are typically used for protein expression can be used. Examples of such vectors include pUC19, pUC18, pHSG299, pHSG399, pHSG398, RSF1010, pBR322, pACYC184, pMW219, and so forth.

In order to introduce a recombinant vector containing a SAT gene into a bacterium, methods which are typically used to transform bacteria can be used, such as the method of D. A. Morrison (Methods in Enzymology, 68, 326 (1979)), treating recipient cells with calcium chloride to increase permeability of the cells for DNA (Mandel, M. and Higa, A., J. Mol. Biol., 53, 159 (1970)), and a method based on electroporation.

Furthermore, the SAT activity can also be enhanced by increasing the copy number of the SAT gene. The copy number of the SAT gene can be increased by introducing the SAT gene into a bacterium by using a vector such as those described above, or by introducing multiple copies of the SAT gene onto the chromosomal DNA of a bacterium. Multiple copies of the SAT gene are introduced by homologous recombination which targets a sequence present on the chromosomal DNA in multiple copies. A repetitive DNA or inverted repeat present at the end of a transposable element can be used as a sequence which is present on the chromosomal DNA in multiple copies. Alternatively, as disclosed in Japanese Patent Laid-open No. 2-109985, multiple copies of the SAT gene can be introduced into the chromosomal DNA by incorporating them into a transposon and transferring it.

The bacterium can be obtained by modifying a bacterium belonging to the family Enterobacteriaceae which has L-cysteine-producing ability, such as those described above, so that the activity of the protein encoded by yhaM (henceforth also referred to as "YhaM") is decreased. Alternatively, after such modification so that the activity of the YhaM protein is decreased, L-cysteine-producing ability may be imparted.

The yhaM gene is synonymous with ECK3099, b4470, and yhaN, and it has also been called b3109 or b3108.

The phrase "decrease the activity of the protein encoded by the yhaM gene" means that the activity of the YhaM protein encoded by the yhaM gene is decreased as compared to a non-modified strain, such as a wild-type strain or parent strain, and also means the complete disappearance of the activity.

Modifications to decrease the activity of the YhaM protein are attained by, for example, reducing the expression of the yhaM gene. Specifically, for example, intracellular activity of the protein can be reduced by deleting a part or all of the coding region of the yhaM gene on the chromosome. Furthermore, this gene forms an operon with the yhaO gene (database "Regulon DB", regulondb.ccg.unam.mx/), and the activity of the YhaM protein can also be decreased by reducing the expression, for example, by modifying an expression control sequence of the operon such as a promoter or the Shine-Dalgarno (SD) sequence. Furthermore, the expression of the gene can also be reduced by modifying a non-translated region other than the expression control sequence. Furthermore, the entire gene as well as the sequences on both sides of the gene on the chromosome may be deleted. Furthermore, mutations which cause an amino acid substitution (missense mutation), a stop codon (nonsense mutation), or a frame shift mutation which adds or deletes one or two nucleotides into the coding region of the yhaM gene on the chromosome can be introduced (Journal of Biological Chemistry, 272:8611-8617 (1997); Proceedings of the National Academy of Sciences, USA, 95 5511-5515 (1998); Journal of Biological Chemistry, 266, 20833-20839 (1991)). Furthermore, expression of the yhaM gene can also be reduced by modifying the coding region or a non-coding region of the yhaO gene.

Furthermore, modification can be caused by a conventional mutagenesis based on X-ray or ultraviolet irradiation or the use of a mutagen such as N-methyl-N'-nitro-N-nitrosoguanidine, so long as the activity of the YhaM protein is decreased.

An expression control sequence can be modified for preferably one or more nucleotides, more preferably two or more nucleotides, particularly preferably three or more nucleotides. When a coding region is deleted, the region to be deleted may be an N-terminus region, an internal region, or a C-terminus region, or even the entire coding region, so long as the function of the YhaM protein is decreased or deleted. Deletion of a longer region can usually more surely inactivate a gene. Furthermore, it is preferred that the deleted reading frames upstream and downstream of the region are not the same.

When another sequence is inserted into the coding region of the yhaM gene, the sequence may be inserted into any region of the gene, and insertion of a longer sequence can usually more surely inactivate the gene. It is preferred that the reading frames upstream and downstream of the insertion site are not the same. The other sequence is not particularly limited so long as a sequence which decreases or deletes function of the encoded YhaM protein is chosen, and examples include a transposon carrying an antibiotic resistance gene, a gene useful for L-cysteine production, and so forth.

The yhaM gene on the chromosome can be modified as described above by, for example, preparing a deletion-type version of the gene in which a partial sequence of the gene is deleted so that the deletion-type gene does not produce normally-functioning YhaM proteins, and transforming a bacterium with a DNA containing the deletion-type gene to cause homologous recombination between the deletion-type gene and the native gene on the chromosome, which results in the substitution of the deletion-type gene for the gene on the genome. The protein encoded by the deletion-type gene has a conformation different from that of the wild-type enzyme protein, if it is even produced, and thus the function is reduced or deleted.

Such gene disruption based on gene substitution utilizing homologous recombination is known, and examples include Red-driven integration (Datsenko, K. A, and Wanner, B. L., Proc. Natl. Acad. Sci. USA, 97:6640-6645 (2000)), using a linear DNA in Red driven integration in combination with an excision system derived from λ phage (Cho, E. H., Gumport, R. I., Gardner, J. F., J. Bacteriol., 184:5200-5203 (2002)), using a plasmid containing a temperature sensitive replication origin or a plasmid capable of conjugative transfer, utilizing a suicide vector without a replication origin in a host (U.S. Pat. No. 6,303,383, Japanese Patent Laid-open No. 05-007491), and so forth.

Decrease of the expression of the yhaM gene can be confirmed by comparing the amount of mRNA transcribed from the gene with that in a wild-type strain or unmodified strain. The expression amount can be confirmed by Northern hybridization, RT-PCR (Sambrook, J., Fritsch, E. F., and Maniatis, T. 1989, Molecular Cloning A Laboratory Manual/Second Edition, Cold Spring Harbor Laboratory Press, New York.), and the like.

Decrease of the amount of YhaM protein can be confirmed by Western blotting using antibodies (Molecular cloning, Cold spring Harbor Laboratory Press, Cold Spring Harbor, USA, 2001).

The nucleotide sequence of the yhaM gene of *Escherichia coli* and the amino acid sequence encoded by this gene are shown in SEQ ID NOS: 1 and 2, respectively.

As a result of a domain search of the YhaM protein performed using the search program Pfam, 78 kinds of proteins were retrieved including those derived from or originating from bacteria of the genera *Escherichia, Salmonella* and *Shigella* whose functions are unknown (DUF1063), and therefore it is evident that these proteins are widely conserved in bacteria. Since differences may exist in the nucleotide sequence of the yhaM gene depending on species or strain to which a bacterium belongs, the yhaM gene to be modified may be a variant of the nucleotide sequence of SEQ ID NO: 1. Variants of the yhaM gene can be searched for with BLAST blast.genome.jp/) or the like by referring to the nucleotide sequence of SEQ ID NO: 1. Furthermore, variants of the yhaM gene include genes which can be amplified by PCR using a homologue of the gene, for example, a chromosome of a microorganism such as those of the family Enterobacteriaceae and coryneform bacteria as the template, and synthetic oligonucleotide primers prepared on the basis of the nucleotide sequence of SEQ ID NO: 1.

As examples of yhaM gene homologues from bacteria other than *Escherichia coli*, nucleotide sequences of the yhaM gene of the following bacteria and amino acid sequences are shown in SEQ ID NOS: 20 to 31. Accession numbers in the NCBI (National Center for Biotechnology Information) database are shown in the parentheses (GenBank Identifier(gi)|RefSeq accession (ref)).

*Shigella boydii* Sb227 (accession: gi/82545369|ref|YP_409316.1)

*Citrobacter koseri* ATCC BAA-895 (accession: gi|157148682|ref|YP_001456001.1)

*Salmonella typhimurium* LT2 (accession: gi|16766537|ref|NP_462152.1)

*Actinobacillus pleuropneumoniae* serovar. 3 str. JL03 (accession: gi|165977041|ref|YP_001652634.1)

*Klebsiella pneumoniae* subsp. *pneumoniae* MGH 78578 (accession: gi|152972895|ref|YP_001338041.1|)

*Vibrio fischeri* ES114 (accession: gi|59711248|ref|YP_204024.1|)

The yhaM gene may also encode a protein having a sequence corresponding to the aforementioned amino acid sequence of the YhaM protein, but which includes substitutions, deletions, insertions, additions or the like of one or several amino acid residues at one or several positions.

Although the number of the "one or several" amino acid residues may differ depending on their position in the three-dimensional structure or the types of amino acid residues of the proteins, it is preferably 1 to 20, more preferably 1 to 10, particularly preferably 1 to 5. These substitutions, deletions, insertions, or additions of one or several amino acids are preferably conservative mutations so that the function of the protein is maintained. A conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of conservative mutations are conservative substitutions. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion, etc., may be the result of a naturally-occurring mutation or variation due to an individual difference, or a difference of species of a bacterium.

Furthermore, the gene having such a conservative mutation as mentioned above may be a gene encoding a protein showing a homology of 80% or more, preferably 90% or more, more preferably 95% or more, still more preferably 97% or more, further still more preferably 98% or more, particularly preferably 99% or more, to the entire encoded amino acid sequence, and which has a function equivalent to that of a wild-type YhaM protein. In the present specification, the term "homology" may mean "identity".

The yhaM gene may be a DNA which hybridizes with a probe prepared from known gene sequences, for example, the above described gene sequences or sequences complementary to the sequences under stringent conditions and which encodes a protein which is a functional equivalent to the YhaM protein.

The term "stringent conditions" refers to conditions where a so-called specific hybrid is formed and a non-specific hybrid is not formed. Examples thereof include conditions where DNAs having high homology, for example, at least 80%, preferably 90%, more preferably 95%, more preferably 97%, more preferably 98%, further preferably 99% homology, hybridize with each other and DNAs having homology less than the value do not hybridize with each other; and specifically include conditions corresponding to a salt concentration and temperature of washing which are typical of Southern hybridization, e.g., washing at 60° C., 1×SSC, 0.1% SDS, preferably 60° C., 0.1×SSC, 0.1% SDS, more preferably 68° C., 0.1×SSC, 0.1% SDS, once or preferably twice or three times.

The probe may be a partial sequence of the gene. Such a probe can be prepared by PCR using oligonucleotides prepared based on the known nucleotide sequences of genes as primers, and a DNA fragment containing these sequences as the template. When a DNA fragment of a length of about 300 bp is used as the probe, the conditions of washing after hybridization can be, for example, 50° C., 2×SSC, and 0.1% SDS.

The above descriptions about variants of genes and proteins are similarly applied to enzymes such as serine acetyltransferase and genes coding for them.

<2> Method for Producing L-Cysteine, L-Cystine, Derivatives Thereof, or Mixture Thereof These compounds can be produced by culturing the bacterium obtained as described above in a medium, and collecting L-cysteine, L-cystine, derivatives thereof, or a mixture thereof from the medium. Examples of a derivative of L-cysteine include S-sulfocysteine, a thiazolidine derivative, a hemithioketal corresponding the thiazolidine derivative mentioned above, and so forth.

Examples of the medium used for the culture include ordinary media containing a carbon source, nitrogen source, sulfur source, inorganic ions, and other organic components as required.

As the carbon source, saccharides such as glucose, fructose, sucrose, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia, and so forth can be used.

As the sulfur source, inorganic sulfur compounds, such as sulfates, sulfites, sulfides, hyposulfites, and thiosulfates can be used.

As organic trace amount nutrients, it is desirable to add required substances such as vitamin $B_1$, yeast extract, and so forth in appropriate amounts. Other than these, potassium phosphate, magnesium sulfate, iron ions, manganese ions, and so forth are added in small amounts.

The culture is preferably performed under aerobic conditions for 30 to 90 hours. The culture temperature is preferably controlled to be 25° C. to 37° C., and the pH is preferably controlled to be 5 to 8 during the culture. To adjust the pH, inorganic or organic acidic or alkaline substances, ammonia gas, and so forth can be used. Collection of L-cysteine from the culture can be attained by, for example, any combination of known ion exchange resin methods, precipitation, and other known methods.

L-cysteine obtained as described above can be used to produce L-cysteine derivatives. The cysteine derivatives include methylcysteine, ethylcysteine, carbocysteine, sulfocysteine, acetylcysteine, and so forth.

Furthermore, when a thiazolidine derivative of L-cysteine is produced in the medium, L-cysteine can be produced by collecting the thiazolidine derivative from the medium to break the reaction equilibrium between the thiazolidine derivative and L-cysteine so that L-cysteine is excessively produced.

Furthermore, when S-sulfocysteine is produced in the medium, it can be converted into L-cysteine by reduction with a reducing agent such as dithiothreitol.

EXAMPLES

Hereinafter, the present invention will be explained more specifically with reference to the following non-limiting examples. In the following descriptions, cysteine means L-cysteine.

(1) Cloning of yhaM Gene from *E. coli* MG1655 Strain

By conducting PCR using the chromosomal DNA of *E. coli* MG1655 (ATCC No. 47076) as the template, and the primers ECOyhaM-F (CGCGGATCCAAGATGCCTGC-CGAGAAGATTAACG, SEQ ID NO: 3) and ECOyhaM-R (CGCGGATCCGAGCGAGCTGGAAGCTATCG, SEQ ID NO: 4), a yhaM gene fragment containing 300 bp upstream and 200 bp downstream from the yhaM gene was obtained. Restriction enzyme BamHI sites were designed in the 5' ends of these primers. For PCR, Pyrobest polymerase (Takara) was used, and after a reaction at 94° C. for 5 minutes, a cycle of 98° C. for 5 seconds, 55° C. for 5 seconds and 72° C. for 2 minutes was repeated 30 times in the standard reaction composition described in the protocol of the polymerase to amplify the target fragment. This fragment was treated with BamHI and inserted into pSTV29 (Takara) at the BamHI site in the direction opposite to the direction of the lacZ gene on the vector, to obtain the pSTV-yhaM7 plasmid having a chloramphenicol resistance marker and the cloned yhaM. It was confirmed by sequencing that there was no PCR error.

Then, the amplified fragment was excised from pSTV-yhaM7 with BamHI, and inserted into pACYC177 (Nippon Gene) at the BamHI site in the same direction as that of the kanamycin resistance gene on the vector, resulting in pACYC-M1 with a kanamycin resistant marker. In this way, the plasmids having two different antibiotic resistance markers and cloned with the same yhaM region (both had the same p15A origin) were prepared.

(2) Construction of a yhaM-Enhanced Strain from *E. coli* MG1655 Strain (MG1655/pSTV-yhaM7)

*E. coli* MG1655 was transformed with the pSTV-yhaM7 plasmid constructed as described above to prepare the MG1655/pSTV-yhaM7 strain, which is yhaM-enhanced. Furthermore, a control strain, which was transformed with an empty vector and called MG1655/pSTV29, was also prepared. The transformation of *E. coli* was performed by a conventional method based on electroporation, and selection of the transformants was performed on the LB agar medium (5 g/L of yeast extract, 10 g/L of tryptone, 10 g/L of sodium chloride, 15 g/L of agar) containing an antibiotic corresponding to the antibiotic resistance marker of the plasmid (25 mg/L in the case of chloramphenicol, 20 mg/L in the case of kanamycin).

(3) Construction of a yhaM-Deficient Strain from *E. coli* MG1655 Strain (MG1655ΔyhaM Strain)

Deletion of the yhaM gene was performed by the method called "Red-driven integration", first developed by Datsenko and Wanner (Proc. Natl. Acad. Sci. USA, 2000, vol. 97, No. 12, pp. 6640-6645), and an excision system derived from λ phage (J. Bacteriol., 2002 Sep., 184 (18):5200-3, Interactions between integrase and excisionase in the phage lambda excisive nucleoprotein complex, Cho E H, Gumport R I, and Gardner J F). According to the "Red-driven integration" method, using a PCR product obtained using synthetic oligonucleotides in which a part of a target gene is designed on the 5' side, and a part of an antibiotic resistance gene is designed on the 3' side, respectively, as primers, a gene-disrupted strain can be constructed in one step. By further using the excision system derived from λ phage in combination, the antibiotic resistance gene incorporated into the gene-disrupted strain can be removed. This method for deleting a gene of *E. coli* using the "Red-driven integration" and the excision system derived from λ phage is described in detail in Japanese Patent Laid-open No. 2005-058227, WO2007/119880A1 and so forth. A yhaM gene-deficient strain was also obtained by these same methods.

A DNA fragment having sequences homologous to both ends of the yhaM gene, and with an antibiotic resistance gene (kanamycin resistance gene (Km$^r$)) inserted between them, was obtained by PCR. As for the specific experimental methods and materials, PCR was performed in the same manner as described in Japanese Patent Laid-open No. 2005-058227, except that DyhaM-FW (ATGTTTGATTCGACTT-TAAATCCGTTATGGCAGCGTTACATC-CTCGCCGTTGA AGCCTGCTTTTTTATACTAAGTTG-GCA, SEQ ID NO: 5) and DyhaM-RV (TTATCTGGCCTTGCTCGCCATAATCTC-GATAATCTGCCGATCCGTTTGCTCGC TCAAGTTAG-TATAAAAAAGCTGAACGA, SEQ ID NO: 6) were used as primers, and pMW118-(λ attL-Km$^r$-λ attR) (WO2006/093322A2) was used as the template.

(4) Construction of a Plasmid Carrying an Inhibition-Desensitized Type SAT (Serine Acetyltransferase) Gene (pMIV-CysE5)

It is known that the pMIV-CysE5 plasmid carries the cysE5 gene encoding a mutant SAT which is desensitized to feedback inhibition (U.S. Patent Published Application No. 20050112731(A1)). A cysteine-producing bacterium which produces a marked amount of cysteine can be prepared by introducing this plasmid into the bacterium (U.S. Patent Published Application No. 20050112731(A1), U.S. Pat. No. 5,972,663 etc.). The construction method of pMIV-CysE5 is described below.

The mutant allele *E. coli* cysE gene, cysE5 (U.S. Patent Published Application No. 20050112731(A1)) was obtained by PCR using primers cysEplF (5'-agc-tga-gtc-gac-atg-tcg-tgt-gaa-gaa-ctg-gaa-3', SEQ ID NO: 7), cysER (5'-agc-tga-tct-aga-ata-gat-gat-tac-atc-gca-tcc-3', SEQ ID NO: 8), and the template pMW-PompC-cysE5 (EP1650296A1). A cycle of 94° C. for 0.5 minute was conducted, then cycles of 57° C. for 0.5 minute and 72° C. for 1 minute were repeated 27 times, and then the reaction was maintained at 72° C. for 7 minutes. The cysEplF primer was designed so as to bind with the start codon ATG of the *E. coli* cysE gene and a downstream sequence, and has a 6-mer SalI site at the 5' end. The cysER primer was designed so as to bind with the stop codon of the *E. coli* cysE gene and an upstream sequence, and has a 6-mer XbaI site at the 5' end. A DNA fragment of about 0.7 kb obtained by PCR was digested with SalI and XbaI, and the digestion product was inserted into the pMIV-PompC plasmid which had been similarly digested with SalI and XbaI to construct pMIV-CysE5.

The pMIV-PompC plasmid described above was constructed as follows. By conducting PCR using the genomic DNA of the *E. coli* MG1655 strain as the template, primers PrOMPCF (5'-agc-tga-gtc-gac-aac-cct-ctg-tta-tat-gcc-ttt-a-3', SEQ ID NO: 9) and PrOMPCR (5'-agc-tga-gca-tgc-gag-tga-agg-ttt-tgt-ttt-gac-3', SEQ ID NO: 10), a DNA fragment containing about 0.3 kb of a promoter region of the ompC gene was obtained, and this fragment was inserted into the pMIV-5JS plasmid at the PaeI and SalI sites to construct pMIV-PompC. The plasmid pMIV-5JS was constructed by ligating the BamHI and HindIII sites designed beforehand at both ends of the intJS cassette (described later) with the BglII and HindIII sites of pM12-ter(thr) (described later) (FIG. 1).

Figure 2:
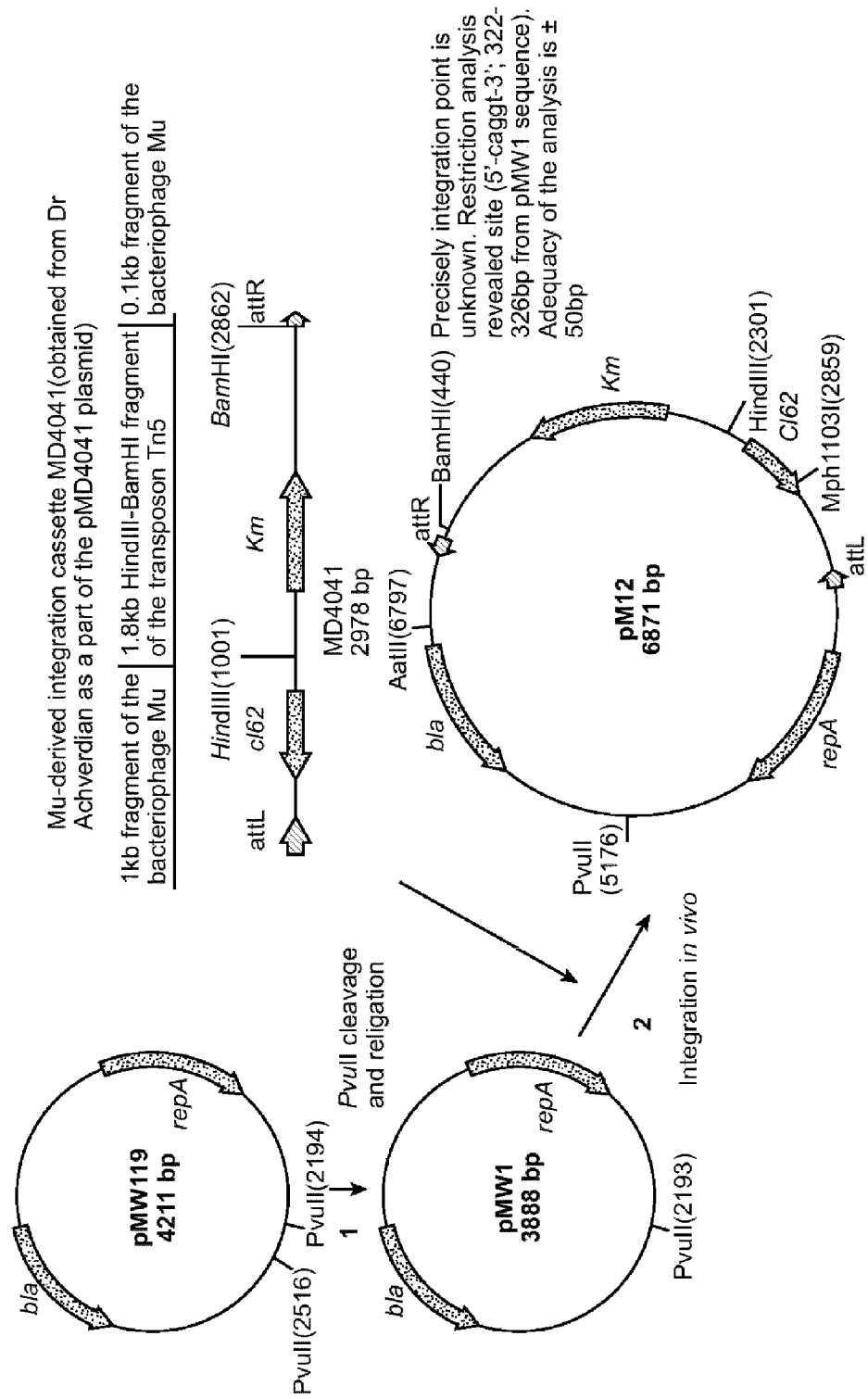
FIG. 2 shows the construction of pM12.
Figure 3:
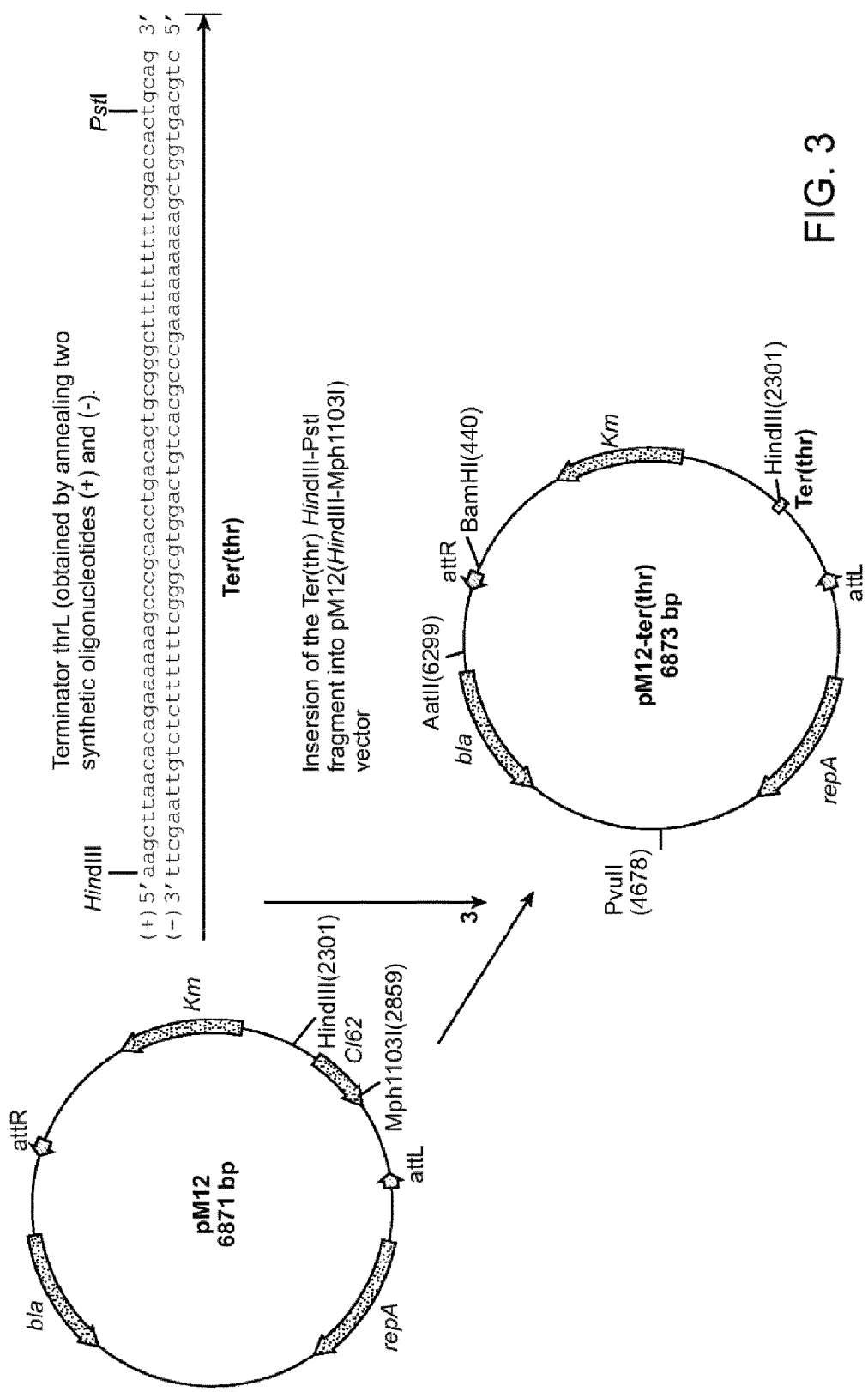
FIG. 3 shows the construction of the pM12-ter(thr) plasmid. The sequences in the drawing are shown as SEQ ID NOS: 11 and 12.
Figure 4:
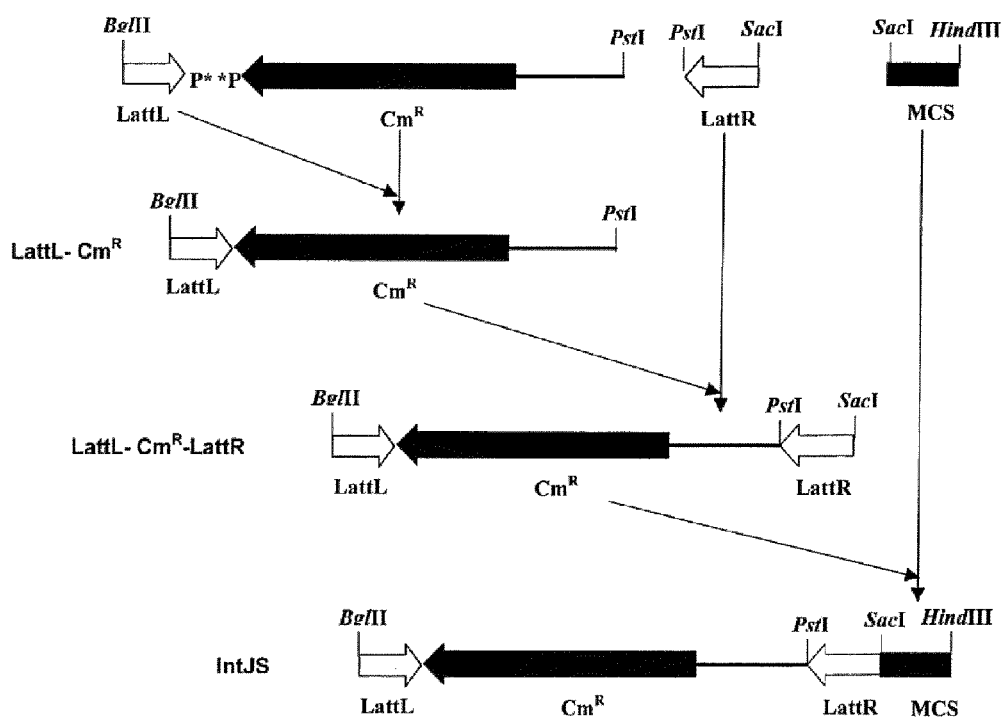
FIG. 4 shows the construction of the IntJS cassette.

The pM12-ter(thr) plasmid was constructed (FIG. 3) by inserting a double stranded DNA fragment (thrL terminator, designed to have HindIII and PstI sites at both ends) produced by annealing a synthetic oligonucleotide (aagcttaaca cagaaaaaag cccgcacctg acagtgcggg cttttttttt cgaccactgc ag, SEQ ID NO: 11) and a complementary synthetic oligonucleotide (ttcgaattgt gtcttttttc gggcgtggac tgtcacgccc gaaaaaaaaa gctggtgacg tc, SEQ ID NO: 12) into the pM12 plasmid which contains the integration cassette derived from Mu phage (EP1486570(A1), FIG. 2) at the HindIII and Mph1103I sites. The IntJS cassette was constructed by the following procedures (a) to (g) (FIG. 4).

(a) By conducting PCR using an upstream primer (ccagatcttg aagcctgctt ttttatacta agttggc, SEQ ID NO: 13, designed to have a BglII site), a downstream primer (gaaatcaaat aatgatttta ttttg, SEQ ID NO: 14, phosphorylated), and the pMW118-attL-tet-attR-ter_rrnB plasmid (WO2005/010175) as the template, a LattL fragment of 0.12 kbp was obtained.

(b) By conducting PCR using an upstream primer (ttacgccccg ccctgccact catcgc, SEQ ID NO: 15, phosphorylated), a downstream primer (gtcactgcag ctgatgtccg gcggtgcttt tgcc, SEQ ID NO: 16, designed to have PstI site), and the pACYC184 plasmid (New England Biolabs) as the template, a $Cm^R$ fragment of 1.03 kbp was obtained.

(c) By conducting PCR using an upstream primer (cagctgcagt ctgttacagg tcactaatac c, SEQ ID NO: 17, designed to have a PstI site), a downstream primer (ccgagctccg ctcaagttag tataaaaaag ctgaacg, SEQ ID NO: 18, designed to have a SacI site), and the pMW118-attL-tet-attR-ter_rrnB plasmid (WO2005/010175) as the template, a LattR fragment of 0.16 kbp was obtained.

(d) By ligation of the LattL and $Cm^R$ fragments, a LattL-$Cm^R$ fragment of 1.15 kbp was obtained.

(e) By ligation of the LattL-$Cm^R$ and LattR fragments digested with PstI, a LattL-CmR-LattR fragment of 1.31 kbp was obtained.

(f) By annealing a synthetic oligonucleotide (cccgagctcg gtacctgcg aatgcatcta gatgggcccg tcgactgcag aggcctgcat gcaagcttcc, SEQ ID NO: 19) with its complementary strand, a double stranded DNA fragment of 70 bp containing a multi-cloning site (MCS) was obtained.

(g) By ligation of the LattL-$Cm^R$-LattR fragment and the double stranded DNA fragment containing a multi-cloning site (MCS), and digested both with SacI, an IntJS fragment of 1.38 kbp was obtained.

(5) Construction of an *E. coli* Strain Having Cysteine-Producing Ability and Enhanced yhaM (MG1655/pMIV-CysE5/pACYC-M1 Strain)

The pACYC-M1 plasmid containing the yhaM gene constructed as described above (kanamycin resistant) was introduced into MG1655 (MG1655/pACYC-M1), along with the inhibition-desensitized type SAT gene-carrying plasmid pMIV-CysE5 (chloramphenicol resistant) to construct an *E. coli* strain having cysteine-producing ability and enhanced yhaM (MG1655/pMIV-CysE5/pACYC-M1 strain). Furthermore, as a control strain, MG1655/pMIV-CysE5/pACYC177 strain was prepared, which was transformed with the empty vector pACYC177 instead of pACYC-M1.

(6) Construction of an *E. coli* Strain with Cysteine-Producing Ability and Deficient in yhaM (MG1655ΔyhaM/pMIV-CysE5 Strain).

The yhaM-deficient strain (MG1655ΔyhaM), constructed as described above, was transformed with the pMIV-CysE5 plasmid to prepare a yhaM-deficient cysteine-producing bacterium, MG1655ΔyhaM/pMIV-CysE5. The MG1655/pMIV-CysE5 strain was prepared as a control, which corresponded to the wild-type strain MG1655 transformed with pMIV-CysE5.

(7) Effect of the Deletion and Enhancement of yhaM on Cysteine Resistance in the *E. coli* MG1655 Strain In order to investigate the influence of the yhaM gene on cysteine resistance, the yhaM-deficient strain MG1655ΔyhaM, the yhaM-amplified strain MG1655/pSTV-yhaM, as well as their respective control strains (MG1655 and MG1655/pSTV29) were each cultured in M9 minimal medium (Sambrook et al., Molecular Cloning, 3rd edition, 2001, Cold Spring Harbor Laboratory Press) which contained cysteine at different concentrations. The difference in cysteine resistance was evaluated by determining change in growth. As the resistance to cysteine increased, the OD of the medium more quickly increased, and as the resistance to cysteine decreased, the OD of the medium increased more slowly. The procedure of the experiment was as follows. Each strain was precultured overnight in M9 minimal medium containing 0.4% of glucose, but no cysteine (3-ml test tube, 37° C., shaking culture), and then inoculated into the main culture medium. At the time of the inoculation, the OD of the preculture was measured, and the amount inoculated was adjusted so that the main culture began with the same amount of cells. The OD at the time of the start of the main culture was about 0.005.

Figure 5:
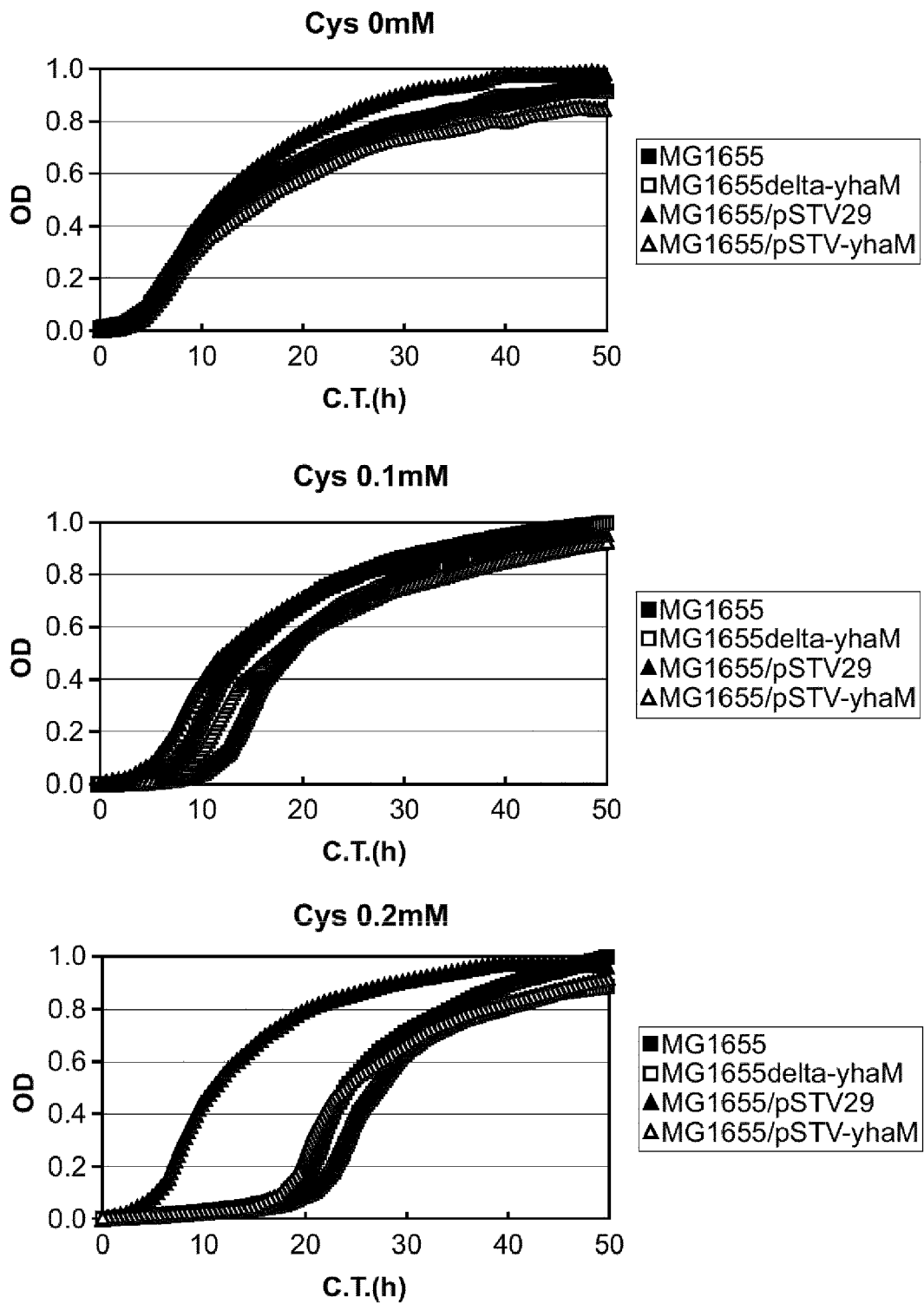
FIG. 5 shows the growth of a yhaM-deficient strain and a yhaM-enhanced strain in the presence of L-cysteine.

The main culture was performed in 4 ml of M9 minimal medium containing cysteine at the following concentrations: 0 mM, 0.1 mM, and 0.2 mM, and 0.4% of glucose using an automatically OD measuring culture apparatus, BIO-PHOTORECORDER TN-1506 (ADVANTEC) and the L-shaped test tube for the apparatus. The progress of the culture (growth curves) is shown in FIG. 5. It was observed that as the concentration of cysteine increased, the OD increased more slowly. However, the yhaM-enhanced strain MG1655/pSTV-yhaM7 grew more quickly as compared to the control MG1655/pSTV29 strain, and it was found to be resistant to cysteine. Furthermore, since the growth of the yhaM-deficient strain MG1655ΔyhaM was slowed as compared to the control MG1655 strain when cysteine was added, it was found that the cysteine resistance thereof had decreased.

(8) Effect of Enhancing yhaM on Cysteine Production in Cysteine-Producing Bacterium In order to investigate the effect of enhancing the yhaM gene on cysteine production, the cysteine-producing abilities of the cysteine-producing bacterium *E. coli* MG1655/pMIV-CysE5/pACYC-M1 in which yhaM was enhanced, and the control MG1655/pMIV-CysE5/pACYC177 strain were compared. For the culture, a cysteine production medium (composition: 15 g/L of ammonium sulfate, 1.5 g/L of potassium dihydrogenphosphate, 1 g/L of magnesium sulfate heptahydrate, 0.1 mg/L of thiamine hydrochloride, 1.7 mg/L of ferrous sulfate heptahydrate, 0.15 mg/L of sodium molybdate dihydrate, 0.7 mg/L of cobalt chloride hexahydrate, 1.6 mg/L of manganese chloride tetrahydrate, 0.3 mg/L of zinc sulfate heptahydrate, 0.25 mg/L of copper sulfate pentahydrate, 0.6 g/L of tryptone, 0.3 g/L of yeast extract, 0.6 g/L of sodium chloride, 20 g/L of calcium carbonate, 135 mg/L of L-histidine monohydrochloride monohydrate, 4 g/L of sodium thiosulfate, 2 mg/L of pyridoxine hydrochloride, 40 g/L of glucose, 25 mg/L of chloramphenicol and 20 mg/L of kanamycin) was used.

The culture was performed according to the following procedures. The MG1655/pMIV-CysE5/pACYC-M1 and the MG1655/pMIV-CysE5/pACYC177 strains were each applied and spread on LB agar medium containing chloramphenicol and kanamycin, and precultured overnight at 37° C. The cells on about 7 cm on the plate were scraped with an inoculating loop of 10 μl (NUNC Blue Loop), and inoculated into 2 ml of the cysteine production medium in a large test tube (internal diameter: 23 mm, length: 20 cm). The amounts of the inoculated cells were adjusted so that the cell amounts at the time of the start of the culture are substantially the same. The culture was performed at 32° C. with shaking. For both strains, after it was confirmed that glucose in the medium had been completely consumed, the culture was ended, and the amount of cysteine which had accumulated in the medium was quantified. The quantification of cysteine was performed by the method described by Gaitonde, M. K. (Biochem. J., 1967 Aug., 104(2):627-33). The experiment was performed in hexaplicate for the both strains, and averages and standard deviations of the accumulated cysteine amounts are shown in Table 1. As shown in Table 1, it was revealed that enhancing yhaM caused a decrease in the accumulation of cysteine.

TABLE 1

| Strain | Gene type | Cys (mg/L) |
| --- | --- | --- |
| MG1655/pMIV-CysE5/pACYC177 | Vector | 64 ± 28 |
| MG1655/pMIV-CysE5/pACYC-M1 | yhaM (plasmid) | 12 ± 6 |

(9) Effect of a Deficiency of yhaM on Cysteine-Producing Ability in Cysteine-Producing Bacterium The cysteine-producing abilities of the yhaM-deficient cysteine-producing bacterium MG1655ΔyhaM/pMIV-CysE5, prepared as described above, and the control MG1655/pMIV-CysE5 strain were compared. For the culture, the cysteine production medium composition was the same as that used in (8) except that kanamycin was not present.

The culture was performed according to the following procedures. The MG1655ΔyhaM/pMIV-CysE5 and the MG1655/pMIV-CysE5 strains were each applied and spread on LB agar medium containing chloramphenicol, and precultured overnight at 37° C. Then, the cells on about 7 cm on the plate were scraped with an inoculating loop of 10 µl (NUNC Blue Loop), and inoculated into 2 ml of the cysteine production medium in a large test tube (internal diameter: 23 mm, length: 20 cm). The amounts of inoculated cells were adjusted so that the cell amounts at the time of the start of the culture are substantially the same. The culture was performed at 32° C. with shaking. After about 15 to 17 hours, it was confirmed that substantially all the glucose in the medium had been consumed (it was confirmed that 95% or more of the total glucose had been consumed), then the culture was ended, and the amount of cysteine which had accumulated in the medium was quantified. The quantification of cysteine was performed by the method described by Gaitonde, M. K. (Biochem. J., 1967 Aug., 104(2):627-33). The experiment was performed in octaplicate for the yhaM-deficient strain and in tetraplicate for the control strain, and averages and standard deviations of the produced cysteine amounts observed in the experiments are shown in Table 2. As shown in Table 2, it was revealed that the deficiency of yhaM caused an increase in the ability of the bacterium to produce cysteine.

TABLE 2

| Strain | Gene type | Cys (mg/L) |
| --- | --- | --- |
| MG1655/pMIV-CysE5 | Vector | 65 ± 4 |
| MG1655ΔyhaM/pMIV-CysE5 | ΔyhaM | 287 ± 61 |

EXPLANATION OF SEQUENCE LISTING

SEQ ID NO: 1: Nucleotide sequence of *E. coli* yhaM gene
SEQ ID NO: 2: Amino acid sequence of *E. coli* YhaM
SEQ ID NOS: 3 to 19: PCR primers
SEQ ID NO: 20: Nucleotide sequence of *Shigella boydii* yhaM gene
SEQ ID NO: 21: Amino acid sequence of *Shigella boydii* YhaM
SEQ ID NO: 22: Nucleotide sequence of *Citrobacter koseri* yhaM gene
SEQ ID NO: 23: Amino acid sequence of *Citrobacter koseri* YhaM
SEQ ID NO: 24: Nucleotide sequence of *Salmonella typhimurium* yhaM gene
SEQ ID NO: 25: Amino acid sequence of *Salmonella typhimurium* YhaM
SEQ ID NO: 26: Nucleotide sequence of *Actinobacillus pleuropneumoniae* yhaM gene
SEQ ID NO: 27: Amino acid sequence of *Actinobacillus pleuropneumoniae* YhaM
SEQ ID NO: 28: Nucleotide sequence of *Klebsiella pneumoniae* yhaM gene
SEQ ID NO: 29: Amino acid sequence of *Klebsiella pneumoniae* YhaM
SEQ ID NO: 30: Nucleotide sequence of *Vibrio fischeri* yhaM gene
SEQ ID NO: 31: Amino acid sequence of *Vibrio fischeri* YhaM While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing a compound selected from the group consisting of L-cysteine, L-cystine, a derivative thereof, and combinations thereof, which comprises culturing a bacterium belonging to the family Enterobacteriaceae in a medium and collecting the compound from the medium,
   wherein said bacterium has L-cysteine-producing ability and has been modified to decrease the expression of the protein encoded by the yhaM gene as compared to the corresponding unmodified bacterium, wherein said expression is decreased by disrupting the yhaM gene, and wherein, prior to modification, the protein is selected from the group consisting of:
   (A) a protein comprising the amino acid sequence of SEQ ID NO: 2, and
   (B) a protein comprising the amino acid sequence of SEQ ID NO: 2 but which includes substitutions, deletions, insertions, or additions of one to 10 amino acid residues, and wherein L-cysteine-producing ability of the bacterium is improved as compared to the corresponding unmodified bacterium.

2. The method according to claim 1, wherein the derivative of L-cysteine is a thiazolidine derivative.

3. The method according to claim 1, wherein, prior to the modification, the yhaM gene is selected from the group consisting of:
   (a) a DNA comprising the nucleotide sequence of SEQ ID NO: 1, and
   (b) a DNA which is able to hybridize with a polynucleotide having a sequence complementary to the nucleotide sequence of SEQ ID NO: 1, or a probe which is prepared from the nucleotide sequence, under stringent conditions comprising washing at 60° C., 0.1×SSC, 0.1% SDS.

4. The method according to claim 1, wherein serine acetyltransferase has been mutated so that feedback inhibition by L-cysteine is attenuated in said bacterium.

5. The method according to claim 1, wherein said bacterium is an *Escherichia* bacterium.

6. The method according to claim 5, wherein said bacterium is *Escherichia coli*.

* * * * *